(12) United States Patent
Bernhardson et al.

(10) Patent No.: US 12,265,072 B2
(45) Date of Patent: Apr. 1, 2025

(54) DEVICES FOR CRUMBLING ROOT CROPS AND DETERMINING THE COMPOSITION THEREOF

(71) Applicant: KWS SAAT SE & Co. KGaA, Einbeck (DE)

(72) Inventors: Duane Bernhardson, Bloomington, MN (US); Elke Hilscher, Einbeck (DE); Frank Friedhoff, Einbeck (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 289 days.

(21) Appl. No.: 18/079,070

(22) Filed: Dec. 12, 2022

(65) Prior Publication Data

US 2023/0115652 A1  Apr. 13, 2023

Related U.S. Application Data

(63) Continuation-in-part of application No. PCT/IB2022/000356, filed on Jun. 27, 2022, and a
(Continued)

(51) Int. Cl.
*G01N 33/02* (2006.01)
(52) U.S. Cl.
CPC .................................. *G01N 33/025* (2013.01)
(58) Field of Classification Search
CPC ............................ G01N 33/025; G01N 21/85
(Continued)

(56) References Cited

U.S. PATENT DOCUMENTS 2,403,910 A  7/1946  Christansen
2,559,551 A  7/1951  Weber
(Continued)

FOREIGN PATENT DOCUMENTS

CZ  305 570 B6  12/2015
DE  26 11 636 B1  3/1977
(Continued)

OTHER PUBLICATIONS

Extended European Search Report Issued EP16192765.2 dated Mar. 21, 2017, 7 pages.
(Continued)

*Primary Examiner* — Omar Flores Sanchez
(74) *Attorney, Agent, or Firm* — Troutman Pepper Locke LLP

(57) ABSTRACT

The invention relates to a device for crumbling root crops into substantially equal sized pieces and homogenizing the flow of crumbled pieces for analysis. The device can have a crumbling device with a main frame and at least one crumbling shaft rotatably supported in the main frame. The crumbling shaft can have a plurality of curved hooks for interlaced movement with recesses in at least one non-rotating cutting rake and at least one cleaning rake. A transport device can move the stream of crumbled root crops from the crumbling device where the stream can be leveled with a leveling rake and compressed into a substantially flat and uniform flow with a roller. The roller can have one or more scrapers positioned to clean the roller surface of residual root crop product and distribute the cleaned material in locations away from the stream to be analyzed to avoid contamination.

21 Claims, 16 Drawing Sheets

Related U.S. Application Data continuation-in-part of application No. 17/689,535, filed on Mar. 8, 2022, now Pat. No. 11,549,928, which is a continuation of application No. 17/104,174, filed on Nov. 25, 2020, now Pat. No. 11,307,188, which is a continuation of application No. 15/288,384, filed on Oct. 7, 2016, now Pat. No. 10,877,014.

(60) Provisional application No. 63/215,090, filed on Jun. 25, 2021.

(58) Field of Classification Search
USPC .......................................... 241/24.26; 436/47
See application file for complete search history.

(56) References Cited

U.S. PATENT DOCUMENTS

| | | | |
|---|---|---|---|
| 2,583,885 | A | 1/1952 | Russenberger |
| 3,726,208 | A | 4/1973 | Brengman et al. |
| 6,998,559 | B2 | 2/2006 | De Baerdemaeker et al. |
| 7,024,942 | B1 | 4/2006 | Jackson et al. |
| 7,223,431 | B2 | 5/2007 | Owens |
| 10,051,787 | B2 | 8/2018 | Todd et al. |
| 10,877,014 | B2 | 12/2020 | Hilscher et al. |
| 2010/0121484 | A1 | 5/2010 | Blanc et al. |
| 2010/0216114 | A1 | 8/2010 | Friedhoff |
| 2016/0082442 | A1 | 3/2016 | Sabol et al. |
| 2020/0316609 | A1 | 10/2020 | Lindner et al. |
| 2021/0148880 | A1 | 5/2021 | Hilscher et al. |

FOREIGN PATENT DOCUMENTS

| | | | | |
|---|---|---|---|---|
| DE | 3313928 | A1 | 10/1984 | |
| DE | 9011121 | U1 | 11/1991 | |
| EP | 0 294 903 | A1 | 12/1988 | |
| GB | 2056880 | A | 3/1981 | |
| WO | 1999/058959 | A1 | 11/1999 | |
| WO | WO-03080249 | A1 * | 10/2003 | ........... B02C 18/142 |

OTHER PUBLICATIONS

Fernandez, B. et al., "Prediction of chemical composition of sugar beet pulp by near infrared reflectance spectroscopy", J. Near Infrared Spectrosc. (2008), vol. 16, pp. 105-110.

Haase, N.U., "Rapid Estimation of Potato Tuber Quality by Near-Infrared Spectroscopy", Starch/Starke (2006), vol. 58, pp. 268-273.

Heppner, S. et al., "Einsatzmoglichkeiten der NIR-Spektrometrie in der Zuckerindustrie Potential applications of NIR spectrometry in the sugar Industry", Zuckerindustrie (2000), vol. 125, No. 5, pp. 325-330.

Ziolko, T. et al., "Relevance of proper sample preparation fo food feed samples for NIR spectroscopy", GIT Laboratory Journal (2002), pp. 268-273 and English Translation thereof.

International Search Report and Written Opinion Issued in International Application No. PCT/IB2022/000356 dated Oct. 21, 2022.

* cited by examiner

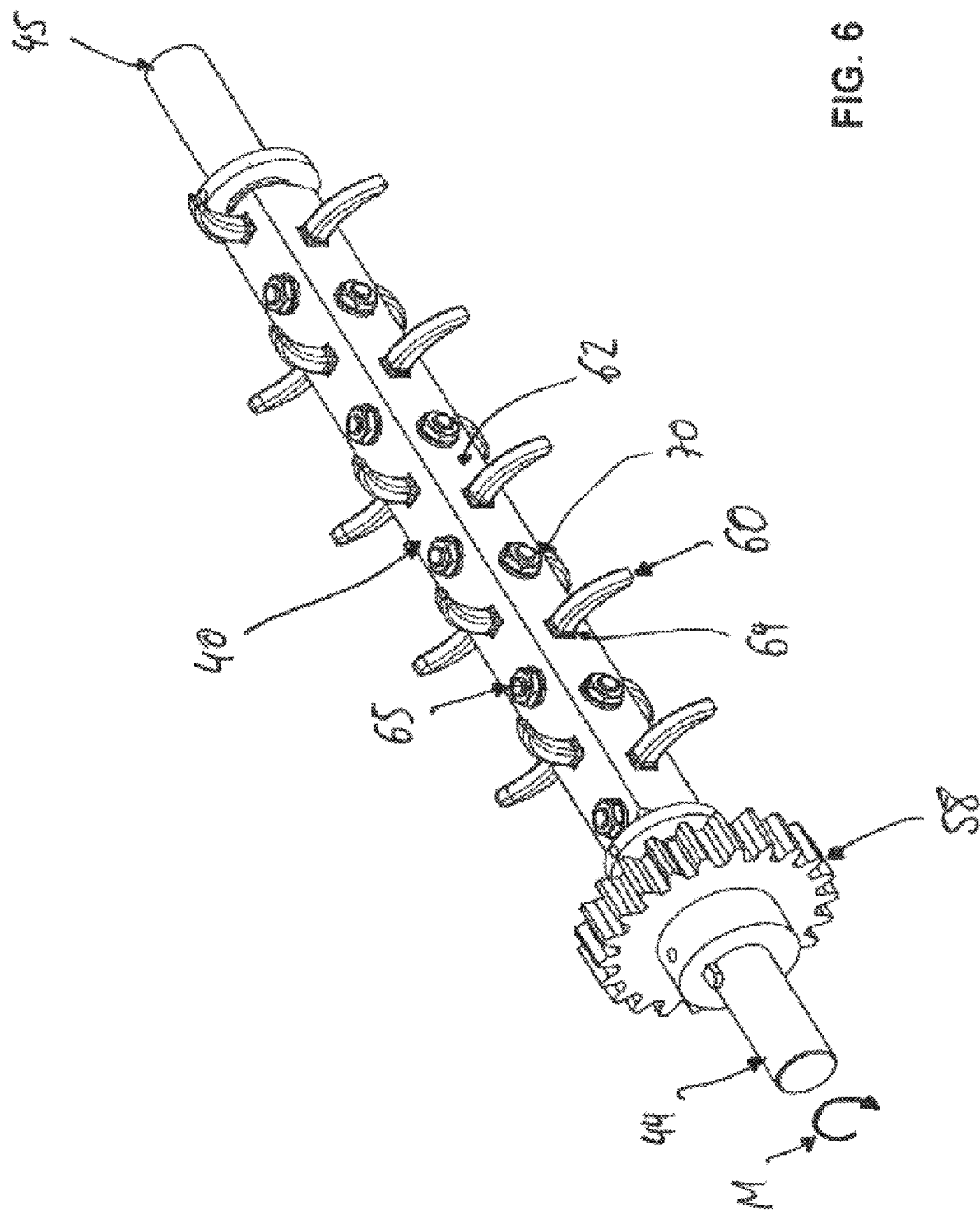

FIG. 10
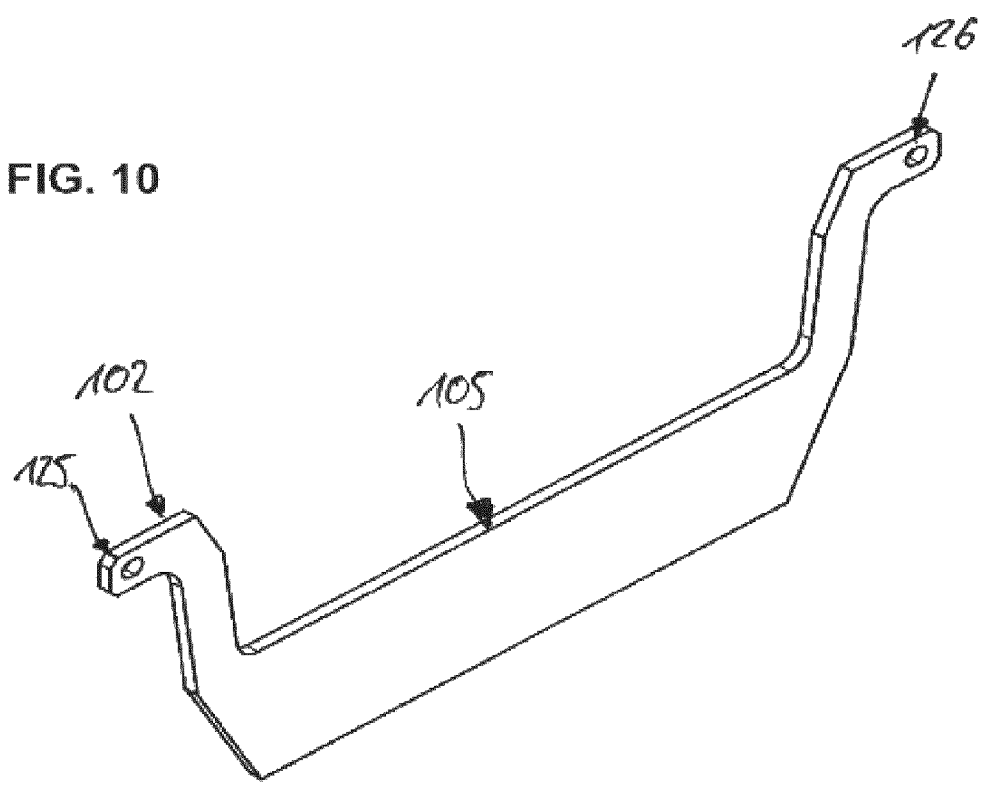
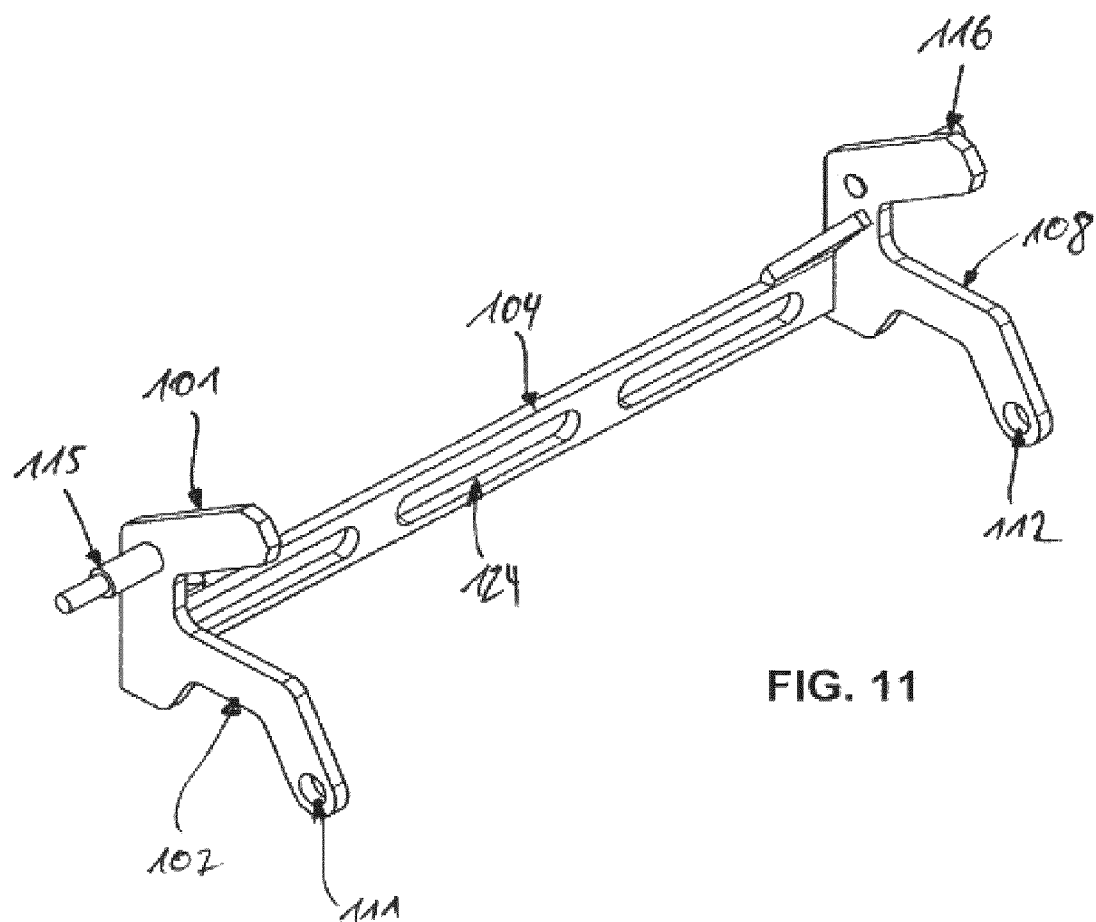
FIG. 11

DEVICES FOR CRUMBLING ROOT CROPS AND DETERMINING THE COMPOSITION THEREOF

CROSS-REFERENCE TO RELATED APPLICATIONS

This application is a continuation-in-part of International Patent Application No. PCT/IB2022/000356, filed Jun. 27, 2022, which claims priority to U.S. Provisional Application No. 63/215,090, filed on Jun. 25, 2021. This application is also a continuation-in-part of U.S. patent application Ser. No. 17/689,535, filed Mar. 8, 2022, which is a continuation of U.S. patent application Ser. No. 17/104,174, filed Nov. 25, 2020, now issued as U.S. Pat. No. 11,307,188 on Apr. 19, 2022, which is a continuation of U.S. patent application Ser. No. 15/288,384, filed Oct. 7, 2016, now issued as U.S. Pat. No. 10,877,014 on Dec. 29, 2020. The disclosures of each of these patents and applications are herein incorporated by reference in their entirety.

TECHNICAL FIELD

The present invention relates to an automated device for crumbling root crops into substantially equal sized pieces and determining components in said root crops.

BACKGROUND

In the cultivation of root crops, measurement of contents plays an important role in economic production, as maximizing yield potential is crucial for efficient use of available arable land. Root crops, for the purposes described herein, can be crops such as sugar beets, fodder beets, red beets, and turnips, as well as tubers such as potatoes, yam, and Jerusalem artichokes. Breeding, cultivation, and processing of root crops involves a continuous, systematic selection and evaluation of suitable root crops with respect to, for example, biomass yield, ingredients, disease resistance, or tolerance to abiotic stresses such as drought. To be able to perform this selection or evaluation, the contents/ingredients of these crops are regularly analyzed for their technical quality for optimal industrial processing. This analysis is associated with a high investment in terms of labor and expense. Ultimately, however, the success of a breeding program is contingent upon the rapid and reliable analysis of the contents of the root crops.

For culturing and experimental trial purposes, root crops are grown in the field in so-called "plots". A plot represents a parcel of land of pre-measured size, and permits the cultivation of several crops, their number providing a statistical indication regarding the nature and distribution of crop yield. In case of sugar beets there are often about 90 beets per plot. The individual plots are rated for productive capacity and, after uprooting, the sugar beets are analyzed for content, which can be influenced by the genotypes as well as a variety of environmental, agronomic, and cultural practices. Such an analysis often takes place using conventional series techniques which provide high accuracy. The goal however is to maximize the efficiency of this process to keep the costs (and waste) of such an analysis to a minimum.

Structure and composition of the sample used for the analysis is crucial for the accuracy of the determined content. In particular, due to genetic, crop cultivation, and environment-contingent influences on growth, significant differences occur from plant to plant in the concentrations of quality-determining ingredients. Furthermore, a non-uniform distribution of concentration of the relevant constituents can also be found within individual root crops such as beets and in the bodies of potato tubers. This heterogeneity of the object of analysis has led to high sampling requirements and the generation of so-called mash samples. Since a mash represents only a sampling of the total population of the crops of a plot, it is representative only to a limited extent. As a result, significant distortions may occur in the measurement of ingredients.

Automated laboratories are typically used to determine ingredients in a serial manner following extraction of pulp samples with aluminum sulfate or lead acetate. Near-infrared spectroscopy (NIRS) has proven to be useful in the analysis of ingredients from crops tested in these analytical laboratories. NIRS is carried out for mashed raw potato samples, potato pulp, beet pulp, technical juices and special byproducts of sugar production from beets (Haase (2006), Starch-Stärke Vol 58 (6), 268-273; Heppner et al. (2000), Sugar Industry, 125 No. 5, 325-330; Fernandez et al. (2008), Journal of Near Infrared Spectroscopy 16,105-110). This spectroscopic method makes it possible to determine several analytes simultaneously in a sample, providing a quick availability of results and avoiding the use of reagents.

The use of NIRS as an analytical measurement method for the determination of ingredients in root crops has often been restricted to an off-site laboratory environment. It therefore has the disadvantages that in addition to the actual analysis, preparatory sample treatment steps are needed which include activities such as harvesting, cleaning, collecting, storage, packing, labeling, freezing, and sending of samples to the investigating laboratory. This process increases the cost and the time required for analysis as a whole.

In an attempt to streamline the determination of ingredients in root crops, NIR spectroscopy has been used for real-time analysis of substances in conjunction with harvesting machines for cereals, maize, and grass (WO 99/58959 A1). Here, a near infrared (NIR) probe composed of a directed light source and sensor is oriented towards the flow of harvested materials. In practice, however, it has been found that a lack of controllability over the chopped materials with this method prior to and during the analysis distorts the analytical results. In addition, most known harvesting machines are not suited for analysis of root crops because the root crops must be crumbled prior to analysis, and the contents of the root crops begin to degrade shortly after crumbling occurs.

US 2010/0216114 A1 shows a process having the following steps: finely dividing the root crops of a plot into substantially equal sized fine pieces, generating a stream of fine pieces of root crop and transporting the fine pieces of root crop with the aid of a transport device, homogenizing or making uniform the stream of fine pieces of a root crop, irradiating the stream of fine pieces of a root crop with light of the near infrared range, recording the reflected radiation, converting the radiation into a spectral signal, and processing the spectral signal for determination of the components.

From the same document, a device for performing the process is disclosed. The device has an apparatus for reducing the root crop to fine pieces, a transport mechanism, a means to equalize a stream of reduced root crops and a measuring instrument for identification and quantification of ingredients. An updated device for the automation of this analysis is disclosed in U.S. application Ser. No. 15/288,384, now U.S. Pat. No. 10,877,014, filed on Oct. 7, 2016 and related U.S. application Ser. No. 17/104,174. The entire contents of these disclosures are incorporated herein by reference in their entirety It has been shown that the structure of the root crop pieces is essential for a subsequent accurate analysis using the NIRS method. Even though certain devices and approaches for can be effective at reducing the root crops to smaller pieces, obtaining a homogenous and even stream of material for consistent and accurate measurement has often been elusive and difficult.

In attempts to resolve these process control challenges; many tests have been carried out. A root crop mill, which is usually used to chop root crops for animal feed production, has been investigated. However, typical mill devices can lack the strength and torque needed to crumble the stream of an entire plot, which can also can result in unevenly sized pieces. A shredding machine has also been tested; with poor results, since the root crop pieces were very uneven and had a high standard deviation in piece size.

Additionally, it has been found that mashed root crop samples and samples containing large cut pieces are difficult to analyze. Tests were carried out with a root crop saw and mill, with the root crops reduced in composition to several consistencies; a normal mash, a coarse mash, juice, large pieces (e.g. 15-20 $cm^3$), small pieces (3-8 $cm^3$), and slices of ca. 500-800 $cm^3$. When using either the normal mash or coarse mash, the likely fast degradation of the material yielded results which were not exact. When using fine pieces, a small water film often emerged on the pieces which can corrupt the NIRS or THz spectroscopy (terahertz time-domain) measurement, since the water film cannot be penetrated by the radiation. Slices often resulted in a very variable distance between the stream of material and the sensor head when the slices are not evenly cut or are piled upon each other.

Furthermore, particles and pieces of crops can build up in parts of device during reduction and/or transport. If not adequately cleaned, the crumbling, rolling, and transport operations can be subject to sample contamination prior to irradiation.

As a result, there remains a need for improved devices and methods to obtain relatively dry samples that are consistently of uniform size and depth.

SUMMARY

According to an embodiment of the invention, a device for crumbling root crops into substantially equally sized pieces comprises: a main frame having an inlet side and an outlet side; a root crop supply at the inlet side; at least one crumbling shaft rotatable supported in the main frame, the crumbling shaft being provided with a plurality of curved hooks, preferably curved into a direction of rotation of the crumbling shaft; and a non-rotating cutting rake having a plurality of recesses and preferably protrusions and forming a counter-blade for the hooks, wherein the hooks are arranged for interlaced movement with said recesses of the non-rotating rake. The hooks are curved and may have a small axial size compared to the axial length of the respective crumbling shaft. The hooks can have a blade portion at the tip. The rake can also have a sealing function and ensures that only pieces with a size below a certain threshold may pass to the outlet side. The hooks are adapted to crumble pieces of the root crop rather than cutting them. Therefore, the pieces of the root crops remain substantially dry and release little to no moisture during the crumbling process. This crumbling function is in contrast to cutting the root crops, which results in moisture release along the cutting surface and inaccurate infrared or NIRS measurements as described above.

According to another embodiment, the cutting rake is adjustable in height for adjusting a vertical distance to said crumbling shaft. When the distance between the cutting rake and the crumbling shaft is increased, the crumbled pieces of root crop tend to be larger, while a reduced distance leads to smaller pieces of crumbled root crops. Also, the rotational speed of the crumbling shaft may be adjusted for achieving such an effect. In one embodiment, the crumbling shaft is connected to a drive for driving the crumbling shaft, in particular a motor drive. Normally, the crumbling shaft rotates in the range of 300 to 1000 rpm, while a higher rotational speed leads to reduced piece sizes, and vice versa.

In yet another embodiment, the device comprises a cleaning rake adjacent to or opposite the cutting rake for stripping off root crop pieces from the hooks. When the hooks are rotating upwards again, it is desirable that pieces, which are pierced by the hooks, or adhering to the hooks, are stripped off. Moreover, such a cleaning rake also has a sealing effect, such that pieces, which are larger than the recesses between protrusions of the rake, are not able to pass to the outlet.

According to another embodiment of the present invention, the device comprises a de-clogging device for de-clogging clogged root crops from the rake. It may happen that a root crop sticks in the device and is not crumbled anymore, since it may be located at a position where the hooks cannot reach it, or the hooks are blocked by the root crop. It may also happen that the root crop is cut at one place by the hooks and the hooks only move through the root crop, which does not move anymore, and thus do not crumble off additional pieces. The de-clogging device is operable for de-clogging such root crops and may incorporate one or more elements, e.g. bars, which are movable upwards or any other direction for moving the clogged root crops for bringing them again into a position engageable with the hooks.

According to a further embodiment of the present invention, the device may comprise a set of first and second crumbling shafts supported in said frame, wherein the first and second crumbling shafts are arranged for a counter rotating, wherein one rake is provided between the crumbling shafts having opposingly arranged protrusions and recesses. The rake, which is positioned between these shafts, is the cutting rake. Additionally, two cleaning rakes are preferably arranged at opposite sides distal from the cutting rake.

In yet another embodiment, two sets of such sets of first and second crumbling shafts are arranged side by side, in a parallel manner, such that at least four crumbling shafts are provided in one device.

According to another embodiment of the present invention, a device for determining components in root crops comprises: a device for crumbling root crops into substantially equal sized pieces, the device for crumbling root crops comprises a main frame having an inlet side and an outlet side; a root crop supply at the inlet side; at least one crumbling shaft rotatable supported in the main frame, the crumbling shaft being provided with a plurality of curved hooks, preferably curved into a direction of rotation of the crumbling shaft; and a non-rotating cutting rake having a plurality of recesses and preferably protrusions and forming a counter-blade for the hooks, wherein the hooks are arranged for interlaced movement with said recesses of the non-rotating rake; the device for determining components in root crops further comprises: a transport device for transporting the stream of root crop crumbles; an equalizing roller for homogenizing the stream of root crop crumbles; and a measuring device for identification and quantification of ingredients.

After the crumbed root crop pieces have left the outlet side of the crumbling device, a leveling rake can be positioned to reduce the stream to a more consistent height. The leveling rake can float at an adjustable distance by bolting or otherwise adhering to the stationary frame to define a horizontal plane. The rake can be a flat plate, a substantially L- or U-shaped feature with a lower shelf or surface for refining a consistent downstream flow pattern for the crumbed root crops, or some other shape. The rake can be made or coated with a non-slip material to facilitate passage of the root crop pieces after they have been reduced to a more uniform level.

A roller can be positioned to rotate and compress the root crop samples to further homogenize the stream for analysis. As used herein, the term "homogenize" refers to compressing and shifting the crumbled root crop sample material to increase the quantity and surface area of the sample to be scanned. In some examples, one or more scrapers can be provided on or around the roller and/or the conveyer belt to continuously clean the rolling surfaces and belt during operation to prevent the buildup of crumbled pieces and the contamination of subsequent samples with cleaned material. In a more specific example, a scraper can be provided at an oblique angle to the rolling axis which has a curved arc conforming at least partially with the roller surface to direct any cleaned material away from the stream to be analyzed.

The device can have an apparatus (for example NIR- or THz-spectrometer) with at least a sensor head and a light source which can be used in determining the components in the root crops. A processor can compile the results, and through comparison with calibrated data, the identity and concentrations of the desired crop components can be determined.

In another embodiment of the present invention, a method for determining components in root crops comprises the following steps, in this sequence: crumbling the root crops into substantially equal sized fine pieces using a device for crumbling root crops into substantially equal sized pieces, generating a stream of fine pieces of root crop, and transporting the fine pieces of root crop with the aid of a transporting device; homogenizing or evenly distributing the fine pieces of root crop in a stream; irradiating the stream of fine pieces of root crop with a light of the near infrared range; recording the reflected and/or absorbed radiation; converting radiation into a spectral signal; and processing of the spectral signal for determination of the components. The device for crumbling root crops into substantially equal sized pieces can have: a main frame having an inlet side and an outlet side; a root crop supply at the inlet side; at least one crumbling shaft rotatably supported in the main frame, the crumbling shaft being provided with a plurality of curved hooks, preferably curved into a direction of a rotation of the crumbling shaft; and a non-rotating cutting rake having a plurality of recesses and preferably protrusions and forming a counter-blade for the hooks, wherein the hooks are arranged for interlaced movement with said recesses of the non-rotating rake.

Steps can also be taken to prepare the crumbled root crops exiting the crumbling device so that reliable and consistent results are achieved from analyzing the irradiated material. The homogenizing of the material stream can include one or more leveling apparatus to reduce the stream of crumbled material to a consistent height. The process can also involve using rolling elements to compress and flatten the crumbled pieces into a homogenized stream of sample material so there is less deviation in the amount of radiation absorbed and reflected. The method can also involve cleaning the transporting device, rolling elements, and other components to avoid the buildup of stray material and avoid the potential cross-contamination of future samples to be measured.

The method and steps to determine the root crop contents can be performed in a quality lab, or alternately as part of industrial processing in a factory setting by diverting a stream of root crops from the production facility line. the root crops can be first cut into pieces or cossettes in the factory environment, and then processed to determine the ingredients. Once analyzed, production parameters of the industrial process can be adjusted based on the sample contents, and in many cases the analyzed crumbled pieces can be turned into an industrial product. In another example, the method can be implemented on harvested root crops collected at a piler station, further increasing efficiency by removing the need for an outside quality lab or diversion at a production facility.

Other aspects of the present disclosure will become apparent upon reviewing the following detailed description in conjunction with the accompanying figures. Additional features and/or use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

FIG. 6 is a perspective view of a crumbling shaft comprising curved hooks according to aspects of the present invention;

FIG. 10 is a perspective view of a first de-clogging element according to aspects of the present invention;

FIG. 11 is a perspective view of a second de-clogging element according to aspects of the present invention.

DETAILED DESCRIPTION

Specific examples of the present invention are now described in detail with reference to the Figures, where identical reference numbers indicate elements which are functionally similar or identical. The examples address many of the deficiencies and inefficiencies associated with traditional methods and devices for crumbling and analysing root crops.

Figure 1A:
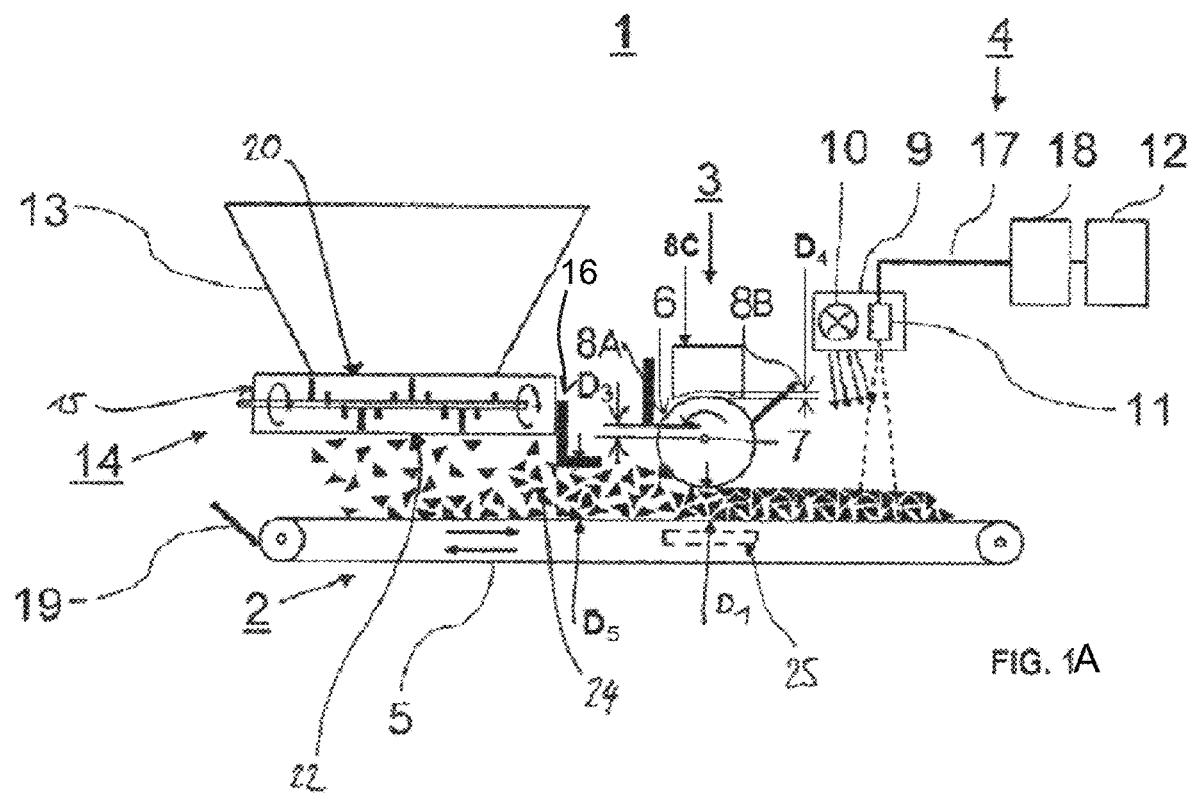
FIG. 1A is a schematic drawing of a device for determining components in root crops according to aspects of the present invention.

Turning to the figures, in FIG. 1A there is a device 1 for determining components in root crops is shown schematically: cleaned root crops of a parcel are collected in a funnel-shaped hopper 13. From the hopper 13, the root crops move to a device 14 for crumbling root crops into substantially equal sized pieces, as it will be described in detail below. In the device 14, the root crops are reduced into essentially even sized pieces. The device 14 comprises a main frame 15 having an inlet side 20 and an outlet side 22. The crumbled root crop pieces 24 fall onto an apparatus for transportation 2, for example a conveyer belt 5, and accumulate there. The speed of the conveyer belt 5 is adjustable and is adapted to the speed at which the root crops are reduced in size and distribution.

Figure 1B:
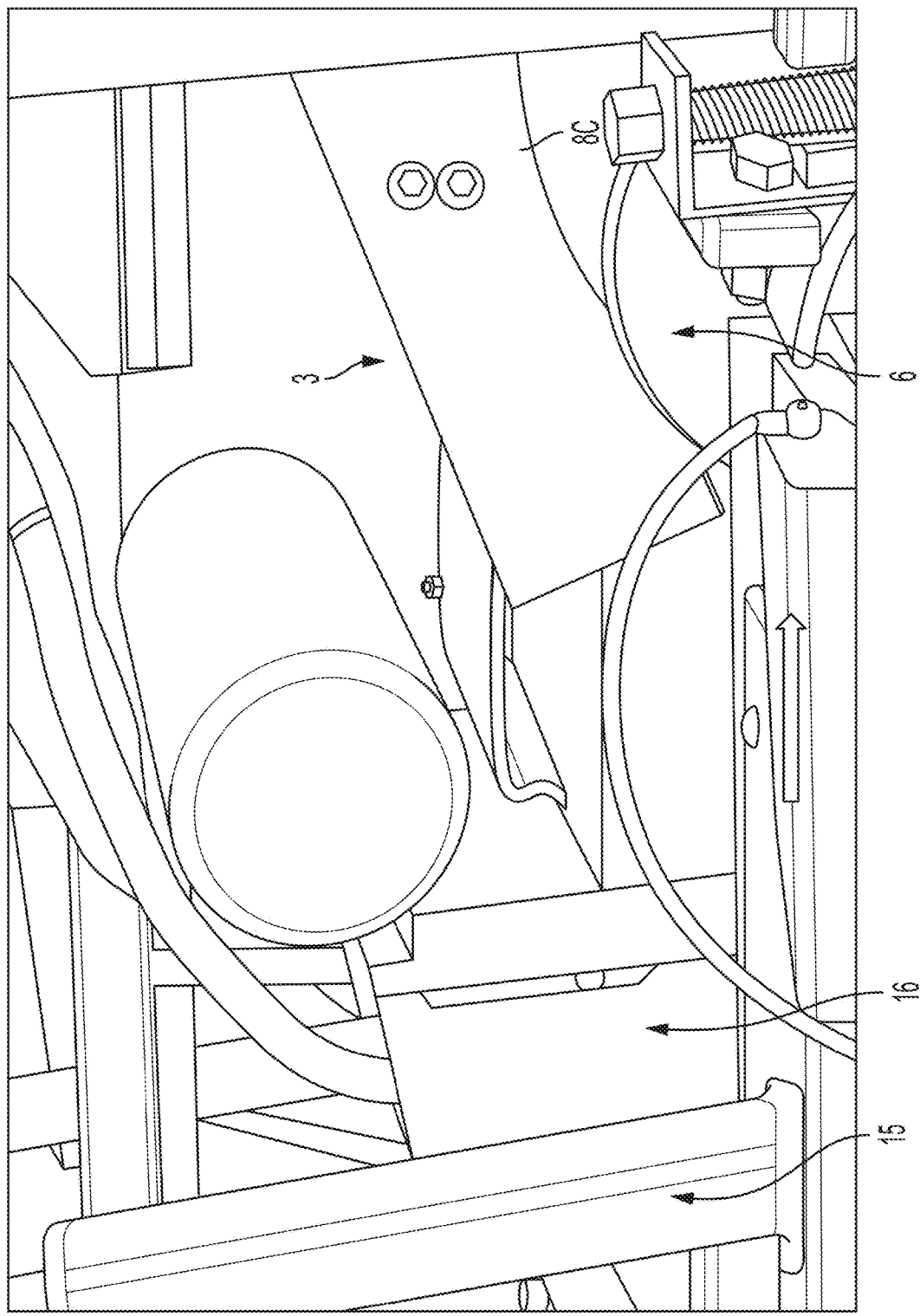
FIG. 1B is a closer view of the device of FIG. 1A according to aspects of the present invention.

However, the accumulation of pieces from the device 14 on the conveyer belt 5 does not result in a smooth surface. On the conveyer belt 5, the accumulated crumbled root crop pieces 24 therefore go into a distribution device 3, which provides a comparatively even distribution of the sample flow. The device 3 has a roller 6 in the form of an elongate shaft, which is arranged at a constant and fixed distance $D_1$ above the conveyer belt 5 along the roll axis 7. Prior to entering the device, a leveling rake 16 can be positioned transversely across the flow on the belt 5 to provide coarse leveling of pieces. The leveling rake 16 can be bolted or otherwise affixed to the device 14 or other portion of the machine frame 15 so that it is suspended at a distance $D_5$ above the belt in the flow path between the outlet side 22 of the crumbling device 14 and the distribution device 3 (FIGS. 1A and 1B). Crumbled root crop pieces 24 traveling in an uneven layer in the direction of flow, as shown by the arrow, can be leveled by the leveling rake 16 and better disbursed along the width of the belt 5.

Figure 1C:
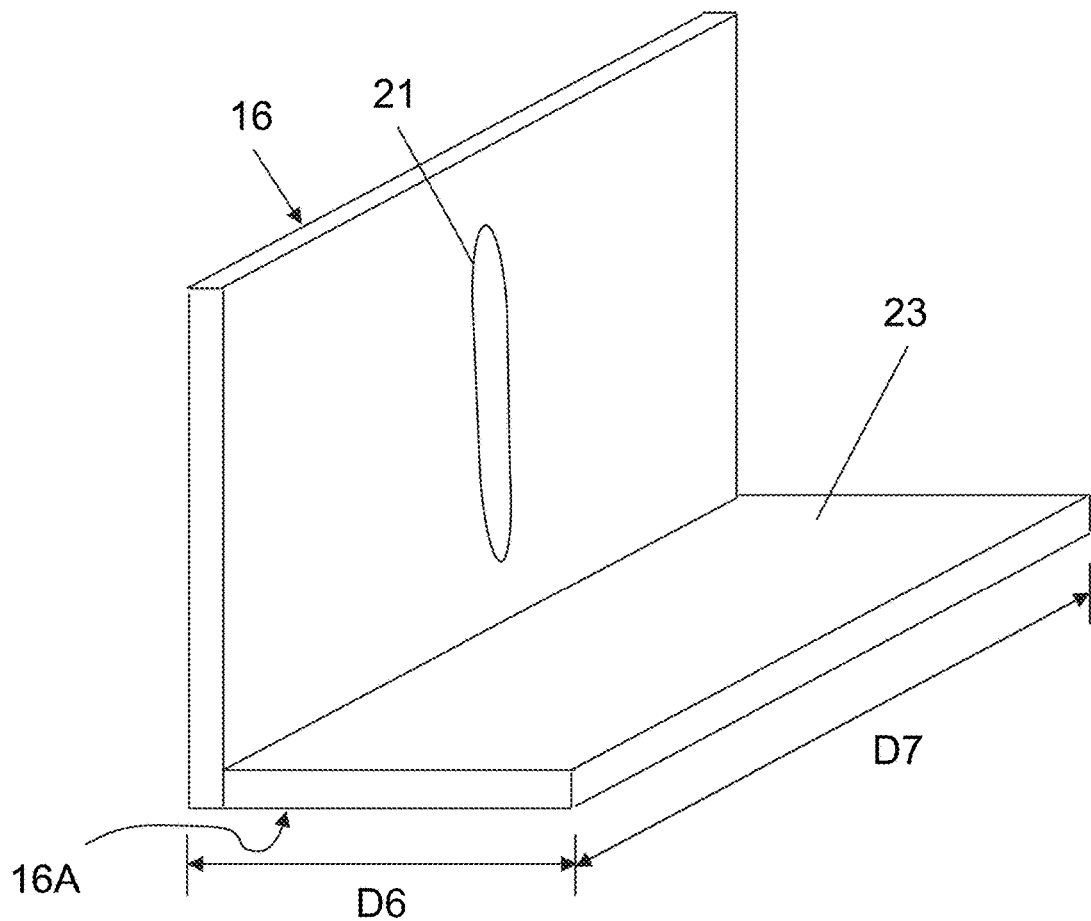
FIG. 1C is a perspective view of a leveling rake of the device of FIG. 1A according to aspects of the present invention.

As shown in FIG. 1C, the leveling rake 16 can have a flat or planar surface 16A in contact with the stream of crumbled root crop pieces 24. The flat surface 16A can be oriented substantially parallel to or at an angle to the plane of the conveyor belt 5. The position of flat surface 16A may be adjusted to be a distance closer to or further away from the conveyer belt 5 to accommodate the flow of crumbled root crop pieces 24. In one embodiment, the leveling rake 16 can have a geometric profile such as the L-shaped cross section depicted in FIG. 1C. In another embodiment, the rake can be a flat plate or a "flattened U"-shaped cross section. In the L-shaped embodiment shown in FIG. 1C, a lower shelf 23 can have a length $D_6$ and width $D_7$ sized to begin refining a consistent downstream flow pattern for the crumbled root crop pieces 24. Shelf 23 can be flat and parallel with the belt 5 or can be beveled or canted to provide a more gradual evening of the sample surface. The leveling rake 16 is a made of a non-slip material, or coated with an anti-slip agent, to prevent build up and carry over of material between samples.

Leveling rake 16 can also have a rear mounting face or bracket having one or more slots 21 for the mounting bolt or bolts (not shown) for adjusting height $D_5$ of the leveling rake 16 above the belt 5. The slot 21 can allow the leveling rake 16 to accommodate a range for height $D_5$ which can be, for example, similar or equal to distance $D_1$ of the roller 6 of the distribution device 3 or up to approximately 75 mm greater than $D_1$. $D_5$ is preferably between approximately 20 mm to 60 mm above or greater than $D^1$, and more preferably between about 25 mm to 40 mm above or greater than $D_1$. Experience has shown a preferred height of approximately 35 mm above or greater than $D_1$ can effectively reduce fluctuations in the distribution of the root crop progression and position the stream more evenly on the belt 5.

Downstream of the leveling rake 16, the roller 6 of the distribution device 3 (see FIG. 1A) can compress the sample stream of crumbled root crop pieces 24 to a certain thickness due to the constant and fixed distance $D_1$ of the shaft above the conveyer belt 5. This compression provides a more flush and refined surface for the efficacy of the measurements to be taken downstream. The distance between the roller 6 and conveyer belt 5 is adjustable; it is preferably between 100 mm and 150 mm.

A motor drives the roller 6 and rotates it in the running direction of conveyer belt 5, as indicated by the arrow. The motor may be driven electrically, hydraulically, or pneumatically. In a preferred embodiment the movement of the roller 6 is coupled with the drive or gearbox of the conveyer belt 5.

As the crumbled root crop pieces 24 contact the roller 6, they are spread on the conveyer belt 5 and are subject to a compressive force as a function of the distance between the roller 6 and the conveyer belt 5. The compressed sample of crumbled root crop pieces 24 thus has a smooth surface and a constant or substantially constant height imparted to it by the roller.

In embodiments of the invention the roller 6 preferably comprises a smooth surface, such as e.g., a polymer surface or a steel surface. The complete roller can be formed of a polymer, or a polymer coating or surface might be provided as a layer on a frame structure of the roller 6. A smooth surface is beneficial for homogenizing the stream. Moreover, it is preferred that the surface has low adhesive features, such as e.g., a non-stick surface or a non-stick coating. In alternative embodiments, additional rollers might be provided, which can be beneficial when the stream of crumbled root crop pieces 24 is large.

Below the belt 5, a block 25 can be provided as a counterpart for the pressure of the roller 6. Block 25 ensures that the belt 5 is not pushed or sagged downwards with respect to FIG. 1A and thus, the stream of crumbled root crop pieces 24 substantially has a height of $D^1$ after passing downstream of the roller 6.

Distribution device 3 may alternatively or additionally comprise a leveling element, such as a rake, bar, plow, or plate in place or in line with roller 6 to make the stream of crumbled root crop pieces 24 more uniform in texture and height.

Measurement data can be contaminated due to material which has clung on the roller 6 and then redistributed into the stream of crumbled pieces. In one example, the distribution device 3 can include one or more scrapers 8A, 8B, and 8C on the roller 6, and/or optionally the conveyer belt 5 may include a scraper 19 provided to continuously clean the roller 6 surface and belt 5 during operation. This avoids the cross-mixing of two root crop samples of consecutively processed plots by ensuring that the cleaned material is not redistributed on top of the stream of a future batch of crumbled pieces. Moreover, a clumping or accumulation of crumbled root crop pieces 24 on the conveyer belt 5 and roller 6 can be avoided, which can otherwise disturb the comparative homogenization of the sample flow.

A scraper 8A can be positioned directly in front of the roller 6 relative to the direction of movement of the conveyer belt 5 to prevent the above-described clumping. For the processing of beets, the optimum distance between rotation axis of the roller and scraper 8A ($D_3$) is around 20 mm. It is particularly preferred that the scraper 8A is cleaning the roller surface above the rotation axis of the roller, i.e., the scraper 8A is positioned or affects the roller surface above the rotation axis 7 of the roller. Scraper 8B can be positioned downstream to clean the roller 6 along a plane approximately tangential to the roller surface.

Figure 1D:
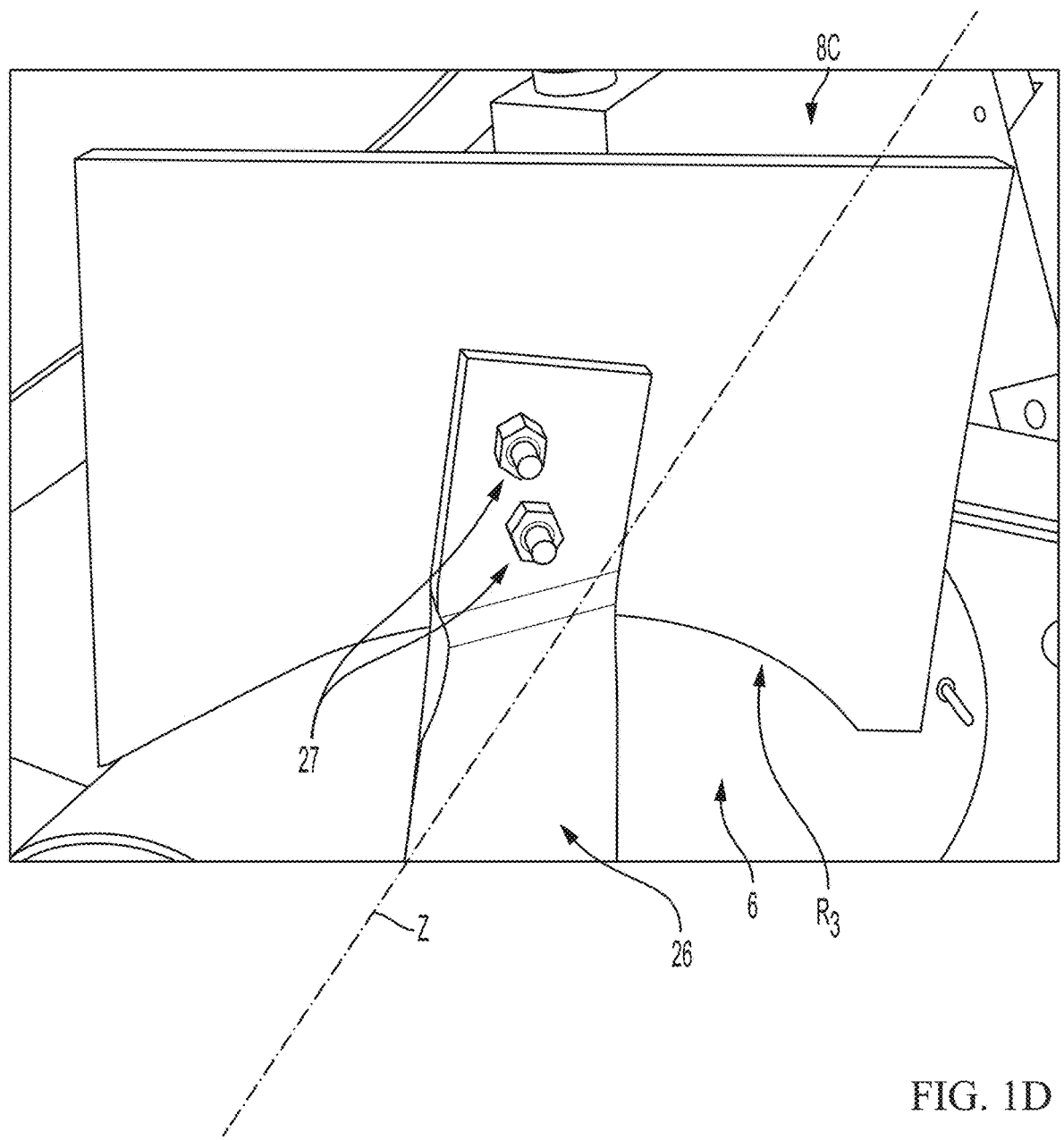
FIG. 1D is a close in view of an oblique scraper of the device of FIG. 1A according to aspects of the present invention.

More preferably, as shown in FIG. 1D, a scraper 8C can be positioned above the roller 6 along a plane oblique to the longitudinal axis z of the roller. Alternatively, the scraper 8C can be positioned at a different clocking angle around the axis if a better distribution is gained without obstructing flow. The design of this scraper can clean the roller and distribute the material on the edge of the stream of the crumbled root crop pieces 24 on the belt 5 in a location or locations that are not irradiated by NIR or viewed by any camera. To conform to the surface of the roller, the scraper can have an edge with an arc of radius $R_3$ which follows the contour of the roller. The radius $R_3$ is primarily dependent on the diameter of the roller and the angle of the scraper. The radius $R_3$ can be in a range, can be equal to the radius of the roller cylinder or can be some other value. In the example shown in FIG. 1D, the arc can have a radius $R_3$ of approximately 150 mm for following the surface of the roller.

Figure 1E:
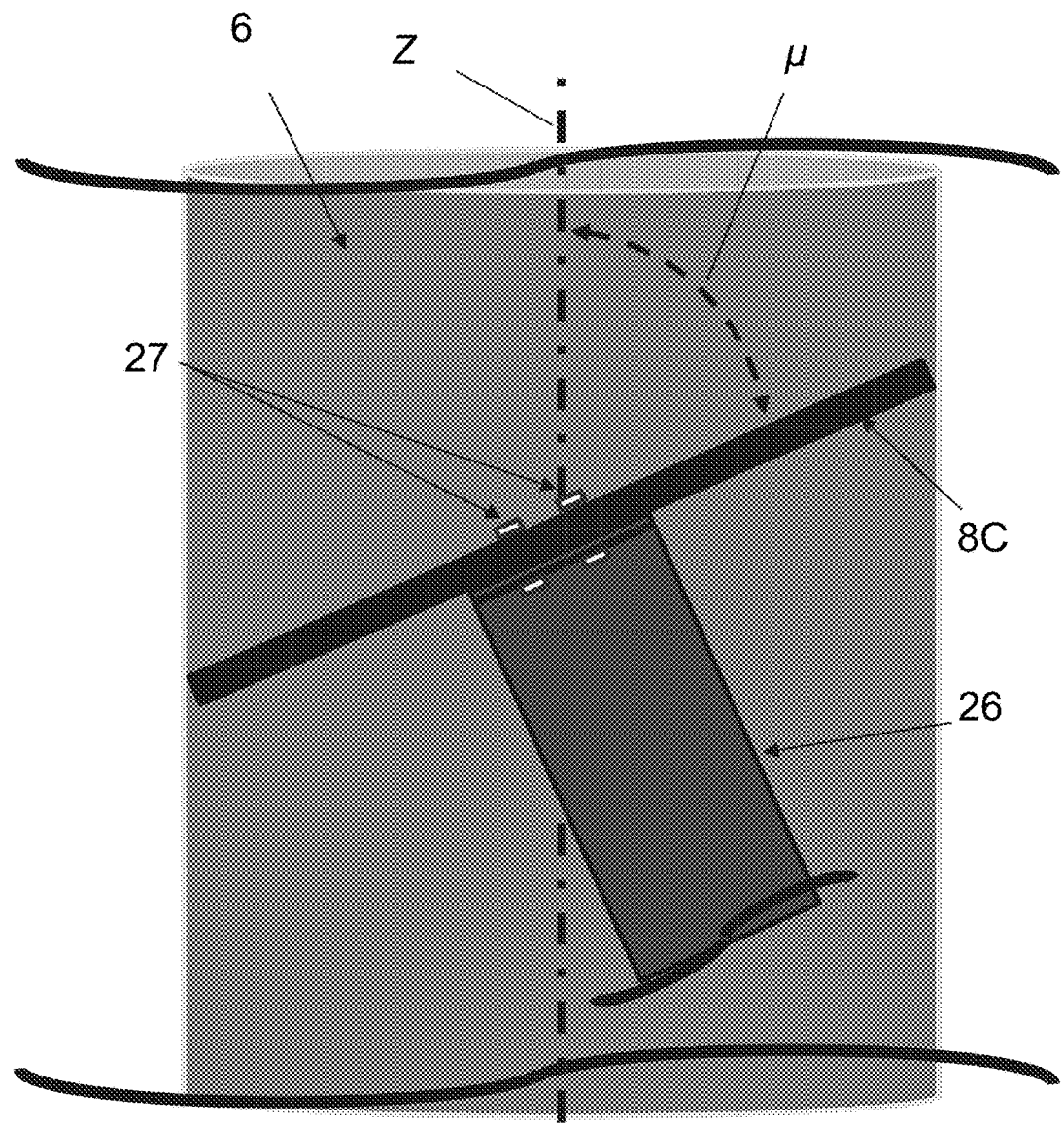
FIG. 1E is a top view of the section of the device with the oblique scraper of FIG. 1D according to aspects of the present invention.

As illustrated in the sectioned top view in FIG. 1E, the scraper 8C can be positioned using a support arm 26 fastened to a stationary component of the device, such as the frame or roller bearing supports. The support arm 26 itself can be stationary or can be adjustable (utilizing a hinge, universal, friction, and/or telescoping mount) to adapt the desired position with respect to the roller 6. The support arm 26 can extend over the roller and have a bracket or other connection for attachment to the scraper 8C. In the examples shown in FIGS. 1D and 1E, bolts 27 are used, but adhesives, welding, and other methods can be appreciated.

The orientation of scraper 8C can be chosen so the scraper acts as a funnel to channel the cleaned material from the roller 6. Angle μ can be selected based on the position of the scraper 8C with respect to the roller so that material is deposited in such a way that contamination of the next root crop sample does not occur. It can be appreciated that a more acute angle μ with respect to axis z will generally result in an increase in radius $R_3$ of the scraper. Similarly, a more obtuse angle μ approaching 90 degrees can typically result in lesser values of $R_3$ converging to the radius of the roller itself. Angle μ can be, for example, between approximately 25 degrees and approximately 40 degrees. Experience has shown that with a radius $R_3$ of approximately 150 mm, a preferred angle μ of approximately 25 degrees is shallow enough to capture material on the full circumference of the roller 6 while being steep enough to deposit a steady stream of cleaned material on the belt 5 beyond the measurement flow.

In other examples, additional oblique scrapers can be positioned along the axis of the roller. Positioning of these scrapers can be determined through monitoring the buildup of accumulating debris and liberating it from the roller into a location on the conveyor belt outside of the range of the measurement stream. In additional examples, suction can be provided in places along the machine to aid in the removal of the cleaned pieces, or channeled grooves can be located just off the belt for their collection.

Referring back to FIG. 1A, directly downstream of the roller 6 is an apparatus for determining components in the more homogenized stream of crumbled root crop pieces 24 (for example NIR- or THz-spectrometer) using e.g., a sensor head 9 with a light source 10 and a sensor 11 for detecting the radiation reflected or absorbed from the smooth surface of the stream of crumbled root crop pieces 24. These analysis methods have been shown to be effective in determining many parameters with a low standard error of prediction in the wavelength range from 850 nm to 1650 nm. In one example, the primary measured parameters are:

Sugar content
Dry Matter
Recoverable sugar
Nitrogen
Marc (insoluble fraction of the root crop)

In addition to the above-mentioned primary measured parameters, the components in sugar beets can be one or several of the following group: total sugar content, content of monosaccharides as glucose; fructose; galactose; content of disaccharides as sucrose, lactose, and maltose; content of Oligosaccharides as raffinose, maltodextrin, and cellodextrin; content of polysaccharides as inulins and fructans; extraction efficiency of sugar; dry matter content, crude protein, crude fiber, amino acids, starch, total sugar content, recoverable sugar content, soluble nitrogen compounds as proteins, betaine, betalain, and amides and amino acids; insoluble nitrogen compounds as insoluble proteins; nitrogen-free organic substances as pectins, saponins, and organic acids; fat content; content of alcohols; phenolic compounds; content of structural carbohydrates as NDF (Neutral Detergent Fiber); ADF (Acid Detergent Fiber); ADL (Acid Detergent Lignin) or content of Hemicellulose; cellulose; Lignin; ash content; content of alkali metal elements and its inorganic compounds as sodium; sodium chloride; content of metal elements and inorganic compounds as calcium; calcium carbonate, magnesium, and magnesium oxide; content of metalloid elements and inorganic compounds as boron, borate minerals, selenium, and silicon; and content of nonmetal elements and inorganic compounds as carbon, carbonates, phosphorus, phosphates; sulfur, and iodine. Additional parameters, such as brix, sugar in molasses, and juicy purity can also be determined.

The sensor head 9 is elevated at a fixed distance of approximately 200 mm to 250 mm above the surface of the smoothed stream of crumbled root crop pieces 24 and can be pivoted as desired relative to the stream of crumbled root crop pieces 24, e.g., in a direction parallel to the conveyer belt or at an angle of approximately 90 degrees. In this way, a user can place and position the sensor to record the entire desired width of the stream of crumbled root crop pieces 24. Alternatively, sensor head 9 may be mounted to a movable assembly, such as a bracket or arm, that can be manually or automatically actuated to adjust the position of the sensor head 9 to maintain a constant distance between the stream of crumbled root crop pieces 24 and the sensor head 9, thereby providing consistent measurements. In one example, a proximity sensor is coupled to sensor head 9 to adjust the position of sensor head 9 based on the thickness or height of the stream of crumbled root crop pieces 24. Such coupling may comprise a separate proximity sensing device or a proximity sensor integrated with the sensor head 9.

The sensor 11 continuously records reflected or absorbed radiation or other data and transmits it via optical fiber 17 to a spectrometer 18, which converts the spectrally resolved radiation wavelengths into digitized portions, at regular intervals of approximately 40 ms. Thus, during the flow-by of the stream of crumbled root crop pieces 24, several hundred such spectra are produced, which are filtered and averaged by a processor 12. By comparison with suitable calibration data, the identities and concentrations of quality-ingredients such as sugar, starch, crude protein, crude ash, crude fiber content, crude fat, anions or cations, NDF (neutral detergent fiber), ADF (acid detergent fiber), (acid detergent lignin), Hemicellulose (HCEL) or Cellulose (CEL) are determined with high precision and are output.

Furthermore, additional types of sensors may be used, such as a proximity sensor to adjust the position of sensor head 9 relative to the stream of crumbled root crop pieces 24; a temperature sensor to measure the temperature of the crumbled root crop pieces 24 to adjust the calibration data; or a color sensor to determine the qualitative state of the crumbled root crop pieces 24, for example to detect a disease state or other optically measurable conditions of benefit.

However, when crops are piled upon each other or not evenly cut throughout the stream, an accurate measurement cannot be obtained. It has been shown in the past that it is important to achieve a substantially homogeneous flow of crumbled root crop pieces 24 with an even and homogeneous particulate stream of uniformly sized pieces and without excessive drainage of liquid from the content. Liquid tends to reflect the light, which makes the determination of components of the root crops more difficult. Therefore, it is important to have a crumbling process which yields a crumbled stream that is relatively free of drained moisture, has even piece size, and a relatively flat surface. A typical moisture content of a whole sugar beet root is about 75% to 80% by weight and retaining a substantial amount of that moisture within the crumbled beet root pieces provides the most accurate analysis. In one embodiment, the stream of crumbled root crop materials has no visible film or accumulation of moisture on the surface of the crumbled pieces. In certain embodiments, the crumbled pieces contain between 65%-80%, preferably 70-80%, and more preferably 75%-80% by weight retained moisture (otherwise not visible on the surface of the crumbled pieces).

Figure 2:
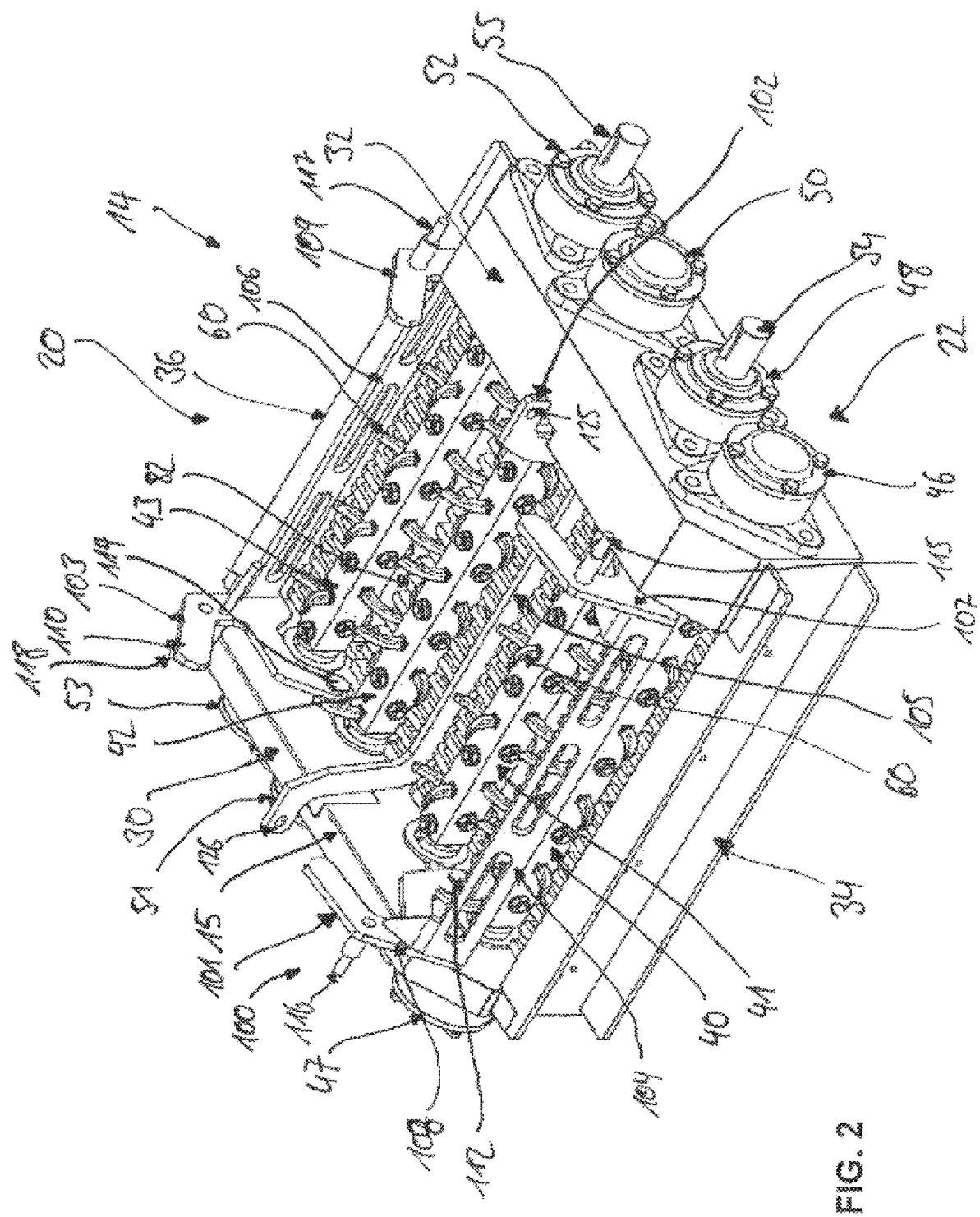
FIG. 2 is a perspective view of a device for crumbling root crops according to aspects of the present invention.
Figure 3:
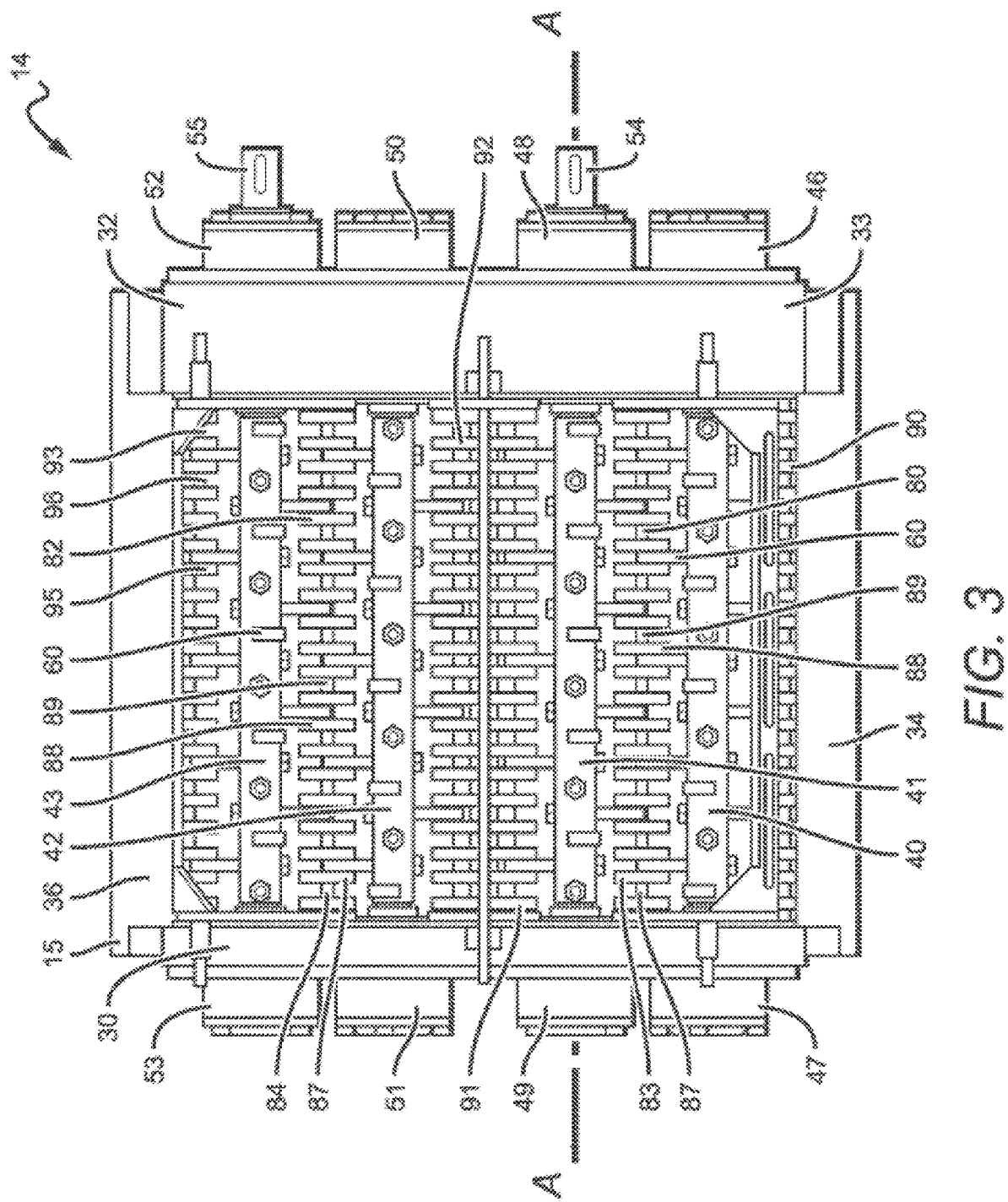
FIG. 3 is a top view of the device of FIG. 2 according to aspects of the present invention.

Providing such a stream is achieved by means of the device 14 for crumbling root crops as shown first in perspective view in FIG. 2 and atop plan view in FIG. 3. The device comprises a frame 15, which is substantially rectangular and comprises first and second head portions 30, 32, which are opposingly arranged and first and second side portions 34, 36, which are also opposingly arranged. All side portions 30, 32, 34, 36 are arranged in a rectangular angle to each other, such that a frame is build. At the inlet side 20, normally a hopper 13 would be placed, which is not shown in FIG. 2 or 3 for simplicity (see FIG. 1A).

In this example shown in FIGS. 2-3, the main frame 15 has four crumbling shafts 40, 41, 42, 43 which are rotatably supported. Axial ends 44, 45 (shown in FIG. 6) of the crumbling shafts 40, 41, 42, 43, are received in bearings 46, 47, 48, 49, 50, 51, 52, 53. The bearings 46, 47, 48, 49, 50, 51, 52, 53 are formed as roller bearings, in particular tilted roller bearings, to support the high forces, which act on the crumbling shafts 40, 41, 42, 43 during crumbling of root crops.

Figure 4:
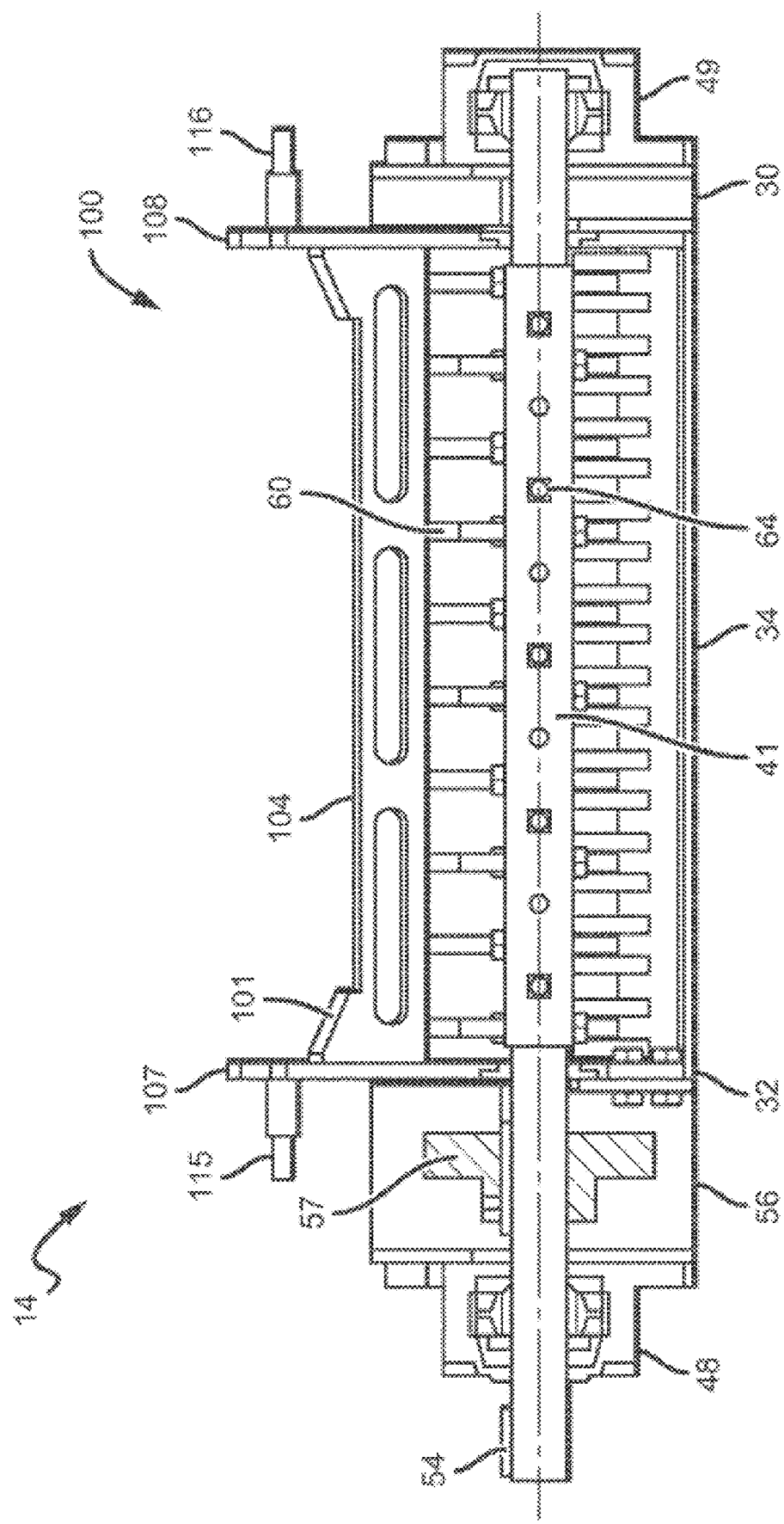
FIG. 4 is a cut through the device of FIGS. 2 and 3 according to aspects of the present invention.

Two of the four crumbling shafts 40, 41, 42, 43 form one set. The shafts 40, 41 can form a first set of crumbling shafts and shafts 42, 43 can form a second set of crumbling shafts. Only one crumbling shaft 41, 43 of each set of crumbling shafts is provided with a drive shaft extension 54, 55, protruding through the respective bearing 48, 52 and engageable with a corresponding drive shaft of a drive motor or the like. Within a housing portion 33 of the second head panel 32, a gearbox can house gearing 56 for each set of crumbling shafts 40, 41, 42, 43 (gearing 56 can be seen in FIG. 4). Gearing 56 comprises a first gearing wheel 57 mounted on the crumbling shaft 41, which engages a second gearing wheel 58 fixed to crumbling shaft 40 (see FIG. 6). By engagement of the two gearing wheels 57, 58, the rotation of crumbling shaft 41 can be transferred to crumbling shaft 40 so that the crumbling shafts 40, 41 of the first set of crumbling shafts synchronously rotate at the same speed. Due to the gearing 56, they rotate in counter rotation. It can be appreciated that an identical gearing setup can be provided within the casing 33 for the second set of crumbling shafts 42, 43. In general, the two sets of crumbling shafts 40, 41 and 42, 43 can be formed identically and the reason for providing four crumbling shafts 40, 41, 42, 43 is mainly to increase volumetric throughput and performance of the device 14.

With reference to FIG. 6, the crumbling shafts 40, 41, 42, 43 (in FIG. 6, only one crumbling shaft 40 is shown; however, the design of the crumbling shafts 40, 41, 42, 43 can be substantially identical) is provided with a plurality of hooks 60 (only one indicated with reference sign in FIG. 6). The hooks 60 can all be formed identical to each other; however, they are preferably positioned offset to each other and about a circumference of the crumbling shaft 40. The crumbling shaft 40 comprises a main shaft portion 62 and the two extensions 45, 44 for being received in respective bearings 46, 47 (FIGS. 2-3). According to this example, the main shaft portion 62 has a rectangular shape having four surfaces being at substantially 90° to each other. The main shaft portion 62 is provided with through bores 64, 65 (FIG. 6) which are arranged in an alternating manner through the main shaft portion 40. That is, the through bores 64, 65 alternate where the first through bore 64 is provided in a first direction and the second through bore 65 clocked 90 degrees in a second direction perpendicular to the first direction of the first through bore 64. The through bores can be parallel to each other and axially offset from each other along the length of the shaft. The offset can be a value in the range of approximately 20 mm to 80 mm, preferably approximately 30 mm to 50 mm, and in this particular instance the offset can be approximately 40 mm. The value may be dependent on the size of the hooks 60 and also on the type of root crop to be crumbled. An offset of approximately 40 mm has been shown to be effective for sugar beets and fodder beets.

Figure 5A:
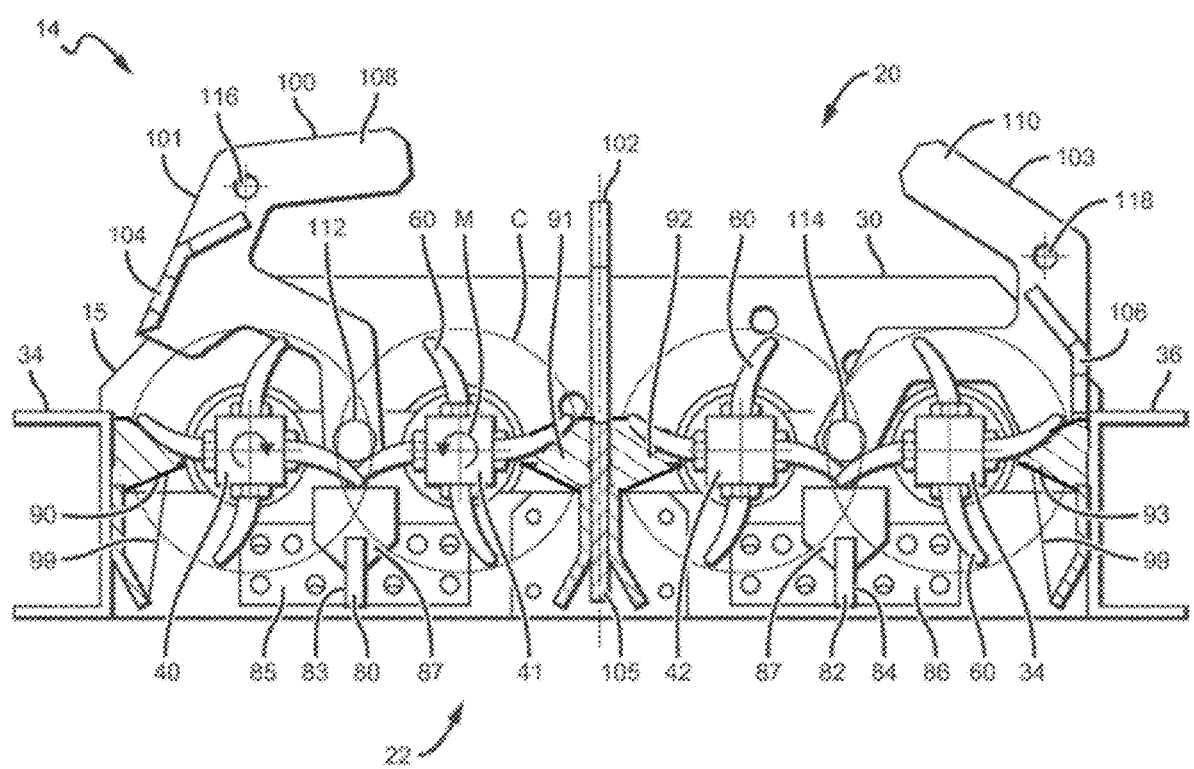
FIG. 5A is a further cut through the device of FIGS. 2 and 3 according to aspects of the present invention.
Figure 7:
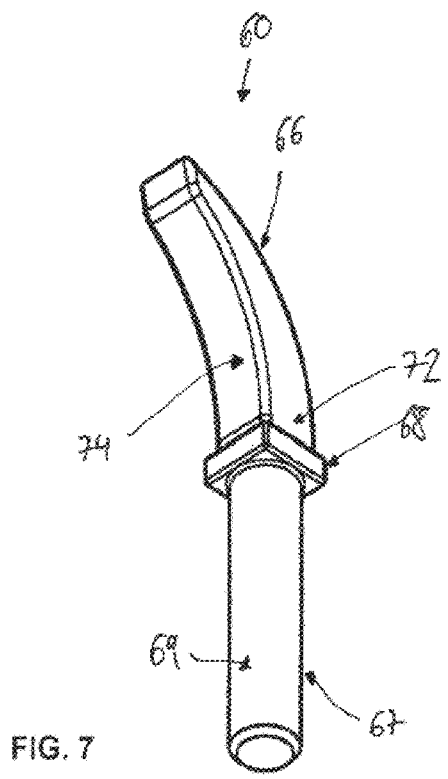
FIG. 7 is a perspective view of a hook according to aspects of the present invention.

The hooks 60 in through bores 64, 65 are also arranged such that they are curved in the direction of rotation of the shaft and are mounted offset or in a staggered orientation relative to the next row of hooks. Each hook 60 comprises a hook portion 66 (see FIGS. 7 and 8) and a mounting portion 67. Between the hook portion 66 and mounting portion 67, a flange portion 68 is provided, which serves as an abutment, when the respective hook 60 is seated in one of the through bore 64, 65. The respective hook 60 is pushed with its mounting portion 67 through the through bore 64, 65 and comes into contact with the main shaft portion 40 with its flange portion 68, such that it is in a defined position. The flange portion 68 can be designed with a square-shaped cross-section as shown in FIG. 7 or alternatively an oval cross-section. This flange portion 68 fits in a respective pressed or milled notch in crumbling shafts 40, 41, 42, 43. The mounting portion 67 is provided with a thread portion 69, which acts together with a nut 70 comprising a correspondingly provided inner threaded portion (see FIG. 6). Each hook 60 is curved into a direction of movement of the respective crumbling shaft 40, 41, 42, 43, as indicated by the moving arrow M (FIG. 5A).

Figure 8:
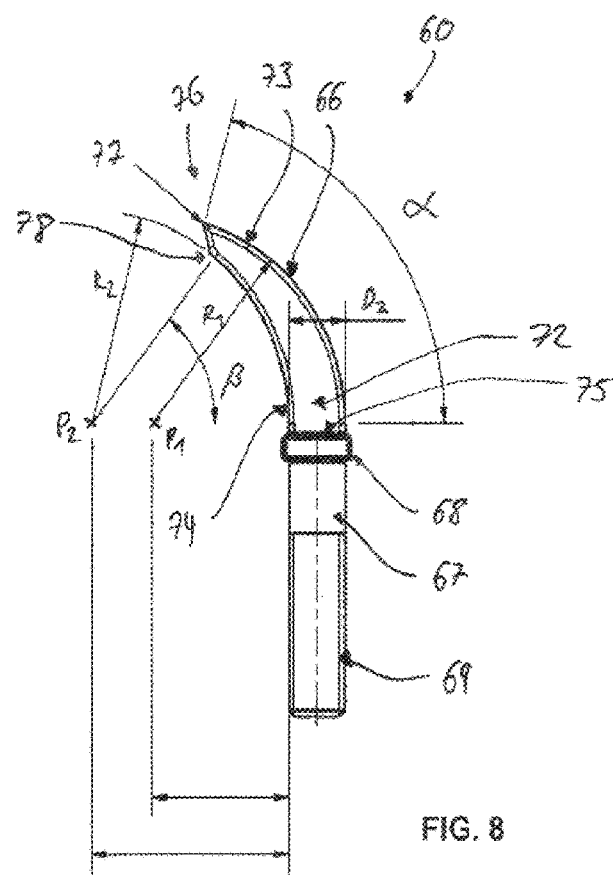
FIG. 8 is a side view of the hook of FIG. 7 according to aspects of the present invention.

The design of the hooks as shown in FIGS. 7 and 8 and will now be described. The hook portion 66 comprises a substantially rectangular cross-section with two parallel side faces 72, as well as a back surface 73 and a front surface 74. The front and back surfaces 73, 74 are curved and resemble an arc of a circle. The radius of the curvature of each of the front and back faces 73, 74 differ from each other and the radius of curvature of the front face 74 is slightly larger than the radius of curvature of the back face 73. This is not absolutely necessary, but beneficial in this example. It shall, however, be understood that it can also be the alternate way in that the radius of the curvature of the back face 73 is larger than the radius of curvature of the front face 74. In this example, the radius $R_1$ of the curvature of the back face is in the range of approximately 20 mm to 40 mm, and more particularly in the range of approximately 34 mm. The radius of curvature $R_2$ of the front face 74 is also in the range of approximately 20 mm to 40 mm, and more particularly in the range of approximately 35 mm. The tapering shape of the hook portion 66 is due to an offset of the center points $P_1$, $P_2$ of each radius $R_1$, $R_2$, which are offset by the thickness $D_2$ of a base portion 75 of the hook portion 66. The thickness $D_2$ is in the range of approximately 5 mm to 15 mm. In the preferred example shown it can be in the range of approximately 10 mm. Thus, the offset between the points $P_1$ and $P_2$ is also about 10 mm, resulting in the tapering shape of the hook portion 66.

At the terminal end 76, the hook portion 66 can have a sharp edge 77 which tapers inwardly and merges via a small protrusion 78 into the front face 74. The edge portion 77 is relatively sharp and comprises a small radius, in particular in the range of approximately 0.1 mm to 0.3 mm. Each hook 60 has a length, when measured from the edge portion 77 to the center of the base portion 75, in the range of approximately 20 mm to approximately 80 mm, preferably approximately 30 mm to approximately 50 mm, and more preferably approximately 40 mm. By this particular arrangement of the hooks 60, the edge portion 77 will cut into the respective root crops, when the crumbling shaft 40, 41, 42, 43 rotates and thus cause brittling, crumbling or ripping off portions of the root crops due to the tapering or wedge shape of the hook 60. When measured in angles α and β of the extension of the partial circular portions formed by the back face 73 and front face 74, the extension of angle α is in the range of approximately 45° to 90°, in particular in the range of approximately 60° to 80°, and more preferably about 75°. Similarly, the extension of the angle β is shorter to provide the wedge portion at the edge portion 77 and is in the range of approximately 30° to 80°, in particular approximately 40° to 60°, and more preferably in the range of about 50°.

Turning back to FIGS. 2 to 5A, when the crumbling shafts 40, 41, 42, 43 rotate, in particular in a counter rotation movement for each set of crumbling shafts 40, 41 and 42, 43, they require a counterpart to provide the reacting force for the root crops to be cut. This counterpart is formed by a cutting rake 80, 82, wherein one cutting rake 80, 82 is provided for each of the first set of crumbling shafts 40, 41 and the second set of crumbling shafts 42, 43. Each cutting rake 80, 82 can be formed to mirror the other and comprises a longitudinal bar 83, 84 extending from the head portion 30 to head portion 32 and attached thereto, by means of a respective mounting plate 85, 86 (see FIG. 5A). By means of these mounting plates 85, 86, the cutting rakes 80, 82 are securely attached to the main frame 15 for stability. The cutting rakes 80, 82 comprise a plurality of metal plates 87 attached to the bars 80, 82, respectively, and offset in axial direction to each other, such that they form protrusions 88 and recesses 89 for cooperating with the hooks 60 on the respective crumbling shafts 40, 41, 42, 43. The protrusions and recesses 88, 89 (see FIG. 3) are provided for interlaced movement with the hooks 60 and provide a counter support or counter blade for the root crops to be cut. Additionally, the protrusions and recesses 88, 89 provide a sieving function, which might be inferred from e.g. FIGS. 3 and 5A, and serve as a filter such that crumbled root crop pieces which remain larger than a specific size are not able to pass to the outlet side 22.

By means of the mounting plates 85, 86, the vertical height of the cutting rakes 80, 82 (see FIG. 5A) can be adjustable. While the cutting rakes 80, 82 are shown in an intermediate position in FIG. 5A, they might be mounted further upwards in a direction towards the hopper, reducing the axial offset with the crumbling shafts 40, 41, 42, 43 such that the size of the crumbled root crop pieces becomes smaller. The cutting rakes 80, 82 can also be attached to a lower portion of main frame 15, such that larger pieces are cut from the root crops. The ultimate bound for this adjustment is limited by the clearance for the cutting circle C, which is a circle connecting the moving point of the edges 77 of the hooks 60. The bar 83, 84 is not able to move further upward, otherwise interference and contact between the edges 77 and the bar 83, 84 would occur.

In addition to the cutting rakes 80, 82, each of the first set of crumbling shafts 40, 41 and second set of crumbling shafts 42, 43 can have two cleaning rakes 90, 91, 92, 93 (see FIG. 5A). The cleaning rakes 90, 91, 92, 93 extend in parallel along the axis of the crumbling shafts 40, 41, 42, 43, and serve as a counterbalance to the cutting rakes 80, 82. The cleaning rakes 90, 91, 92, 93 can be attached to either the head portions 30, 32, or the side panels 34, 36 of the main frame 15 and can be adjustable in height relative to the axis of the cutting rakes. The cleaning rakes 90, 91, 92, 93 are used to clean off stuck or adhered root crop pieces from the hooks 60 as the hooks 60 rotate through the cutting rakes. Cleaning also prevents uncut pieces of the root crops from transiting from the inlet side 20 to the outlet side 22 of the device 14 and positions them for recirculation for crumbling within the device.

Figure 5B:
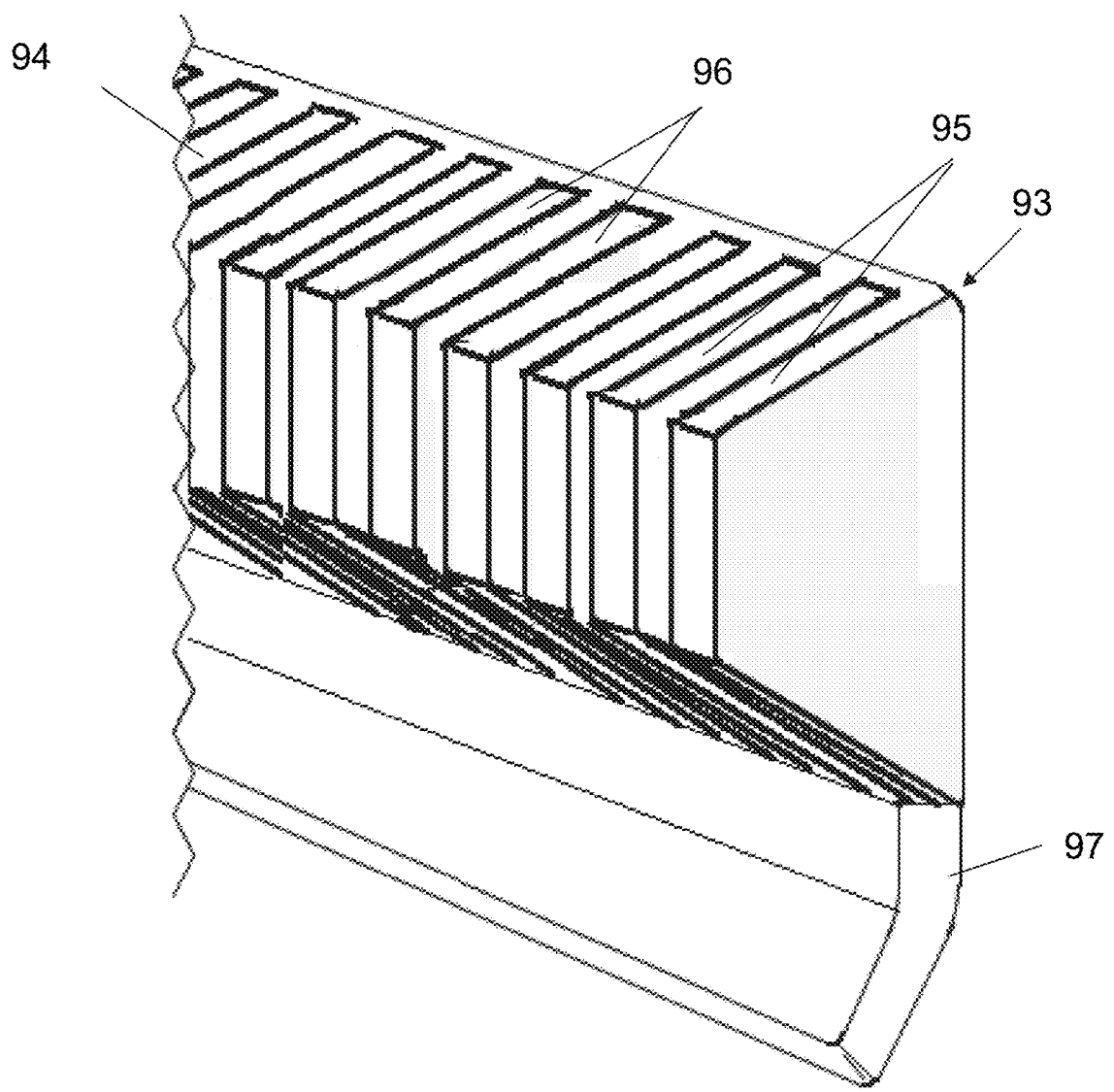
FIG. 5B is a perspective view of a cleaning rake of FIG. 5A according to aspects of the present invention.

Since the cleaning rakes 90, 91, 92, 93 are not subject to very high forces; they can be made from sheet metal or other highly formable material to have a substantially angled shape through punching and bending processes (FIG. 5B). Protrusions 95 and recesses 96 are formed in the cleaning rakes 90, 91, 92, 93 by punching, for interlaced movement with the hooks 60, when the crumbling shafts 40, 41, 42, 43 rotate. In a preferred embodiment the cleaning rakes 90, 91, 92, 93 are stabilized by gusset plates 99 fixed by welding as indicated in FIG. 5A.

Figure 5C:
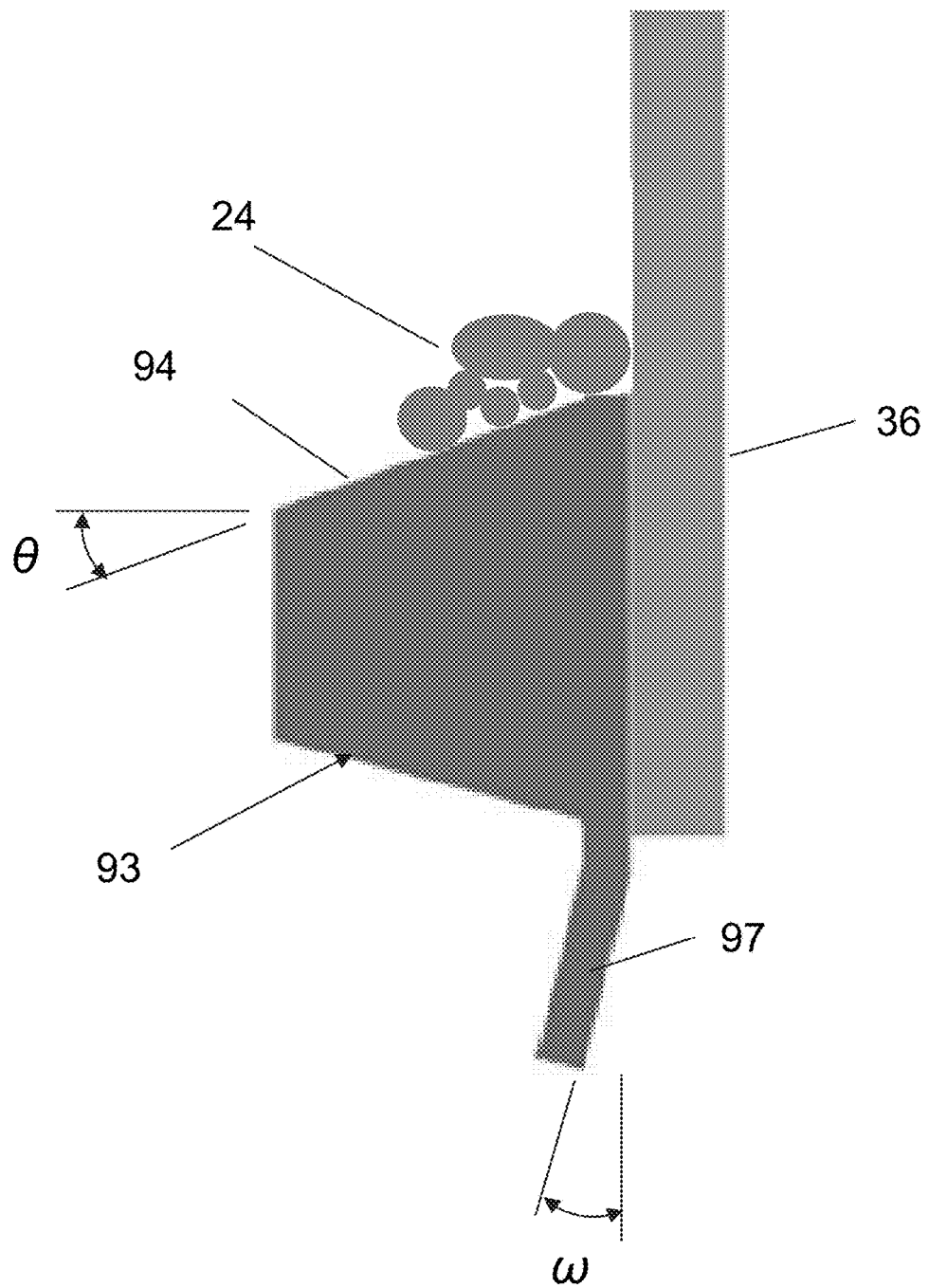
FIG. 5C is a side view of a cleaning rake of FIG. 5A according to aspects of the present invention.

The angled shape of the cleaning rakes 90, 91, 92, 93, as illustrated further in FIGS. 5B and 5C, facilitates the recirculation of root crop pieces which have not yet been reduced in size sufficiently to join the measurement stream. The comb 94, or upper surface of the cleaning rake 93 can be sloped with respect to the horizontal plane. The slope makes it difficult for residual crumbled root crop pieces 24 to build up on the comb 94 near the side panel 36 of the frame and to minimizes the potential for carry over to contaminate future samples. The angle θ formed by the comb 94 with respect to the horizontal can be in a range of approximately 30° to 60° and more preferably in the range of about 45°.

Similarly, the cleaning rakes 90, 91, 92, 93 can have an angled lower toe portion 97 designed to deflect and collect pieces or crumbled root crops onto a common, centralized portion of the conveyor belt 5. This collection process aids in ensuring all of the crumbled flow to be sampled interacts with and passes under the leveling rake 16 at the outlet side 22 of the crumbling device 14. The angle ω as shown in FIG. 5C formed by the toe portion 97 with respect to the vertical need not be steep but helps to ensure material does not collect in peripheral areas and that cut pieces can be homogenized and processed by the leveling and rolling operations downstream.

In the event one or more of the root crops to be crumbled get stuck or clogged, the device 14 of the present designs can contain a de-clogging device 100. This de-clogging device will now be described with reference to FIGS. 2, 5A, 9, 10 and 11 in particular. The de-clogging device 100 is operable for removing clogged root crops from the cutting rakes 80, 82 or cleaning rakes 90, 91, 92, 93. According to this particular example, in which the device 14 has the two sets of crumbling shafts 40, 41, 42, 43, the de-clogging device 100 has three de-clogging elements 101, 102, 103, where the second de-clogging element 102 is used for both sets of crumbling shafts 40, 41, 42, 43. The first and third de-clogging elements 101, 103 can be substantially formed identical to each other, but arranged mirrored and opposite to each other. Each of the de-clogging elements 101, 102, 103 is arranged to be movable adjacent to a cleaning rake 90, 91, 92, 93. There can also be additional de-clogging elements for de-clogging root crop pieces which are clogged to the cutting rake 80, 82. However, experience has shown that root crop pieces primarily get clogged at either the connecting portion between the first and second sets of crumbling shafts 40, 41, 42, 43 and side panels 34, 36 and at the cleaning rakes 90, 91, 92, 93, since there is less cutting action than at the cutting rakes 80, 82. For a complete cutting of all root crop pieces provided to the inlet side 20, it is necessary that the root crops are able to "dance" on the crumbling shafts 40, 41, 42, 43. If too many root crop pieces are loaded into the hopper 13, pressure on the rakes 80, 82, 90, 91, 92, 93 can cause them to become clogged.

According to the present example, the de-clogging element 102 is at a central portion and the de-clogging elements 101, 103 are at the side panels 34, 36. Each of the de-clogging elements 101, 102, 103 can have a bar 104, 105, 106 with a longitudinal extension parallel to said crumbling shafts 40, 41, 42, 43 and movable upwards for raising clogged root crops or root crop pieces.

The outer de-clogging elements 101, 103 can have respective brackets 107, 108, 109, 110, between which the bar 104, 106 extends and to which the bar is attached. The brackets 107, 108, 109, 110 are pivotally attached to the head portions 30, 32 via respective pivot hinges 111, 112, 113, 114, which are substantially arranged vertically above the cutting rakes 80, 82, respectively. The de-clogging elements or pivot hinges can also be positioned at other positions within the scope of the invention.

At the brackets 107, 108, 109, 110, engagement pins 115, 116, 117, 118 are attached which extend outwardly away from their respective brackets. The engagement pins 115, 116, 117, 118 are provided for engagement with an activation piston 119, 120 (see FIG. 9). The activation piston 120 is attached to a fixed portion 122 and is able to contract with respect to the right-hand side of FIG. 9 to a retracted position as shown by piston 119 attached to fixed portion 121 in the left-hand side of FIG. 9. When the pistons 119, 120 retract, the de-clogging elements 101, 103 are pivoted about the pivot hinges 111, 112, 113, 114 and thus the bars 104, 106 are raised in an arc-shaped path starting from the respective cleaning rakes 90, 93 upwardly towards the center of the device 14 in the direction of the rotating crumbling shafts 40, 43. The bars 104, 106 are moreover provided with respective through holes 124 (shown in FIG. 11) or slots for increasing friction between the clogged root crop pieces and the bar 104, such that the clogged root crop pieces can be transported in a central direction and thus be again engaged by means of the hooks 60.

Figure 9:
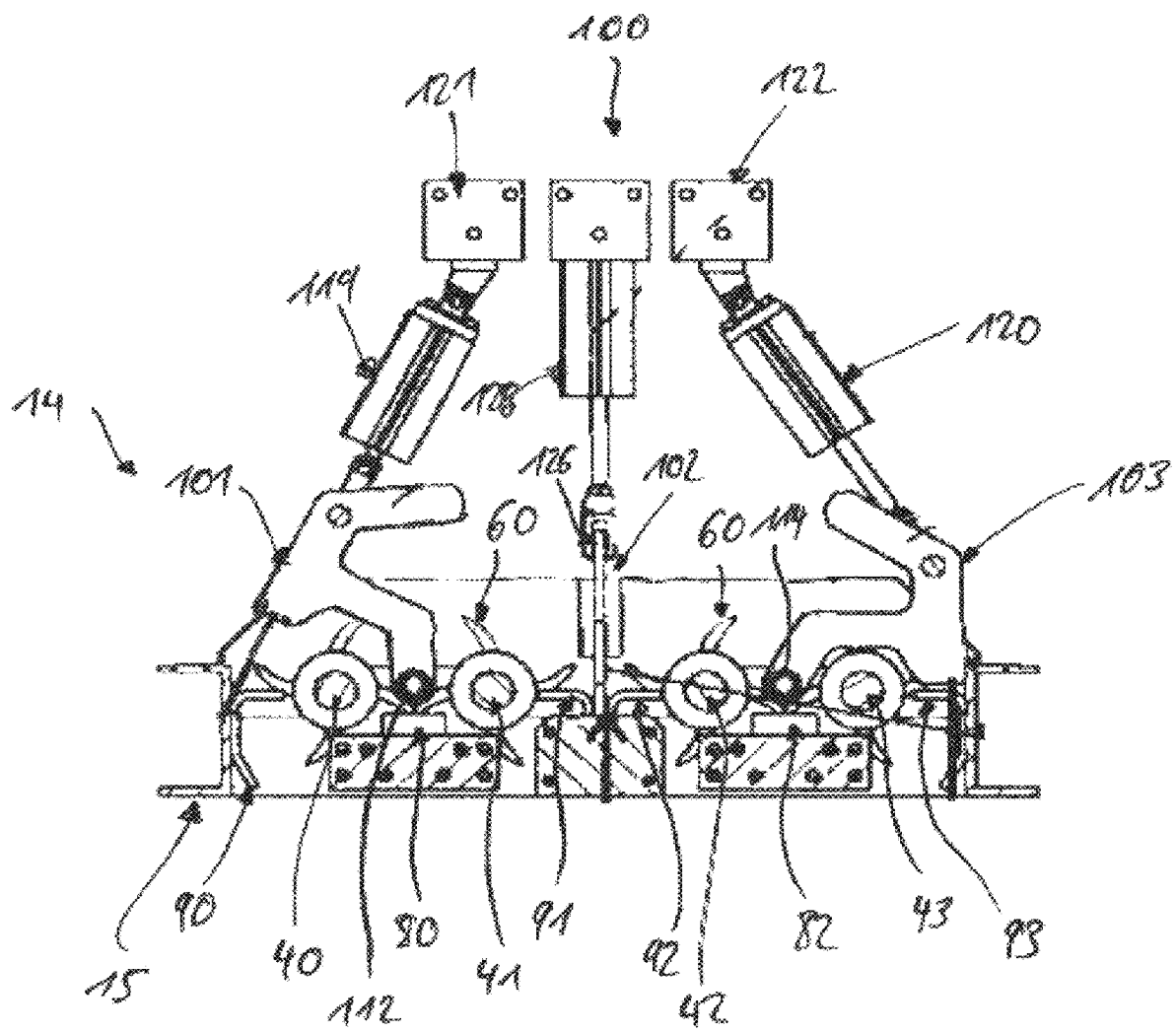
FIG. 9 is a further cut through the device for crumbling root crops according to aspects of the present invention.

The central de-clogging element 102 acts in a similar manner. It can have engagement portions 125, 126 (see FIG. 10), which are engaged by a third pair of pistons 128 (only one is shown in FIG. 9; it shall be understood there is a second one for engagement section 125 on the opposite side of the device). These pistons 128 can be activated in a parallel manner, such that the whole of de-clogging element 102 is lifted upwards. Alternately, they can be activated in sequence such that the de-clogging element 102 is pivoted and portion 125 is raised and lowered again, followed by the raising and lowering of portion 126. This also leads to clogged root crop pieces being pushed towards the center of the device 14.

Figure 12:
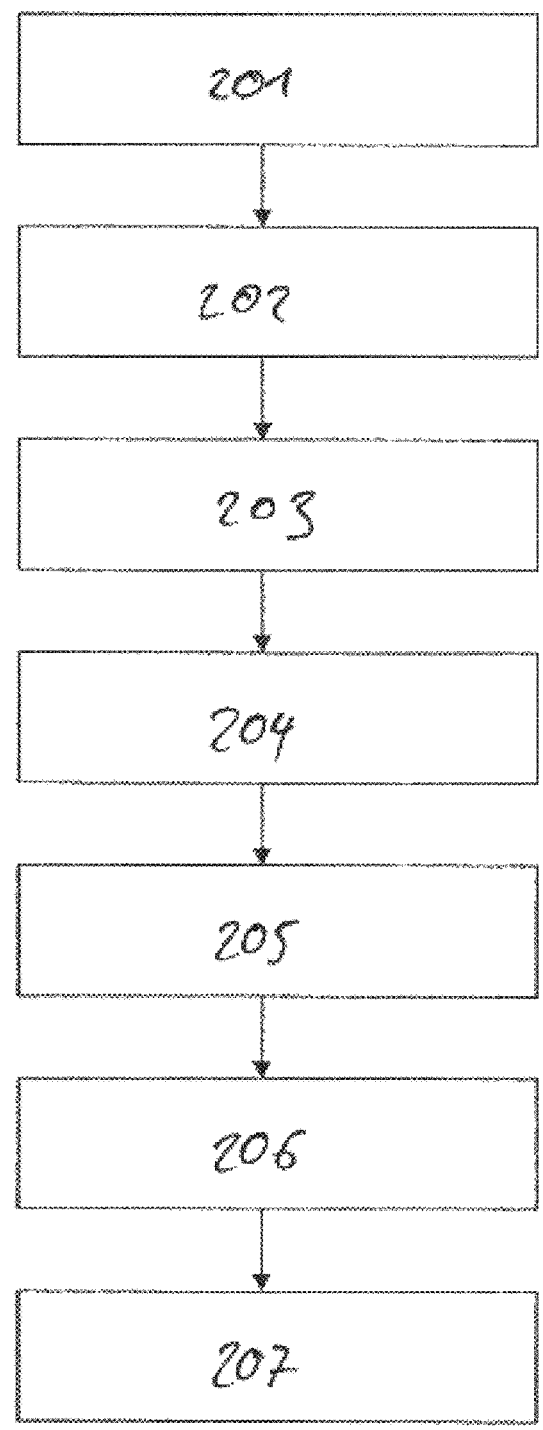
FIG. 12 is a flowchart of a method for determining components in root crops according to aspects of the present invention.

FIG. 12 illustrates a method 200 for determining components in root crops, with reference made to components in the other figures. The method can begin with the step 201 of crumbling the root crops into substantially fine, equal sized pieces using the device 14, as described previously. As the root crops are fed into the hopper 13, the crumbling shafts 40, 41, 42, 43 are activated to rotate and root crop pieces exit at the outlet side 22. Preferably, the crumbling shafts are rotated at a speed of approximately 300 to 1000 rpm, wherein a higher rotational speed can result in smaller pieces of root crops and a lower rotational speed can result in larger pieces.

In the second step 202, a stream of crumbled root crop pieces 24 is generated and transported with the aid of a transporting device 5. Afterwards, the stream on the transporting device can be leveled by way of a leveling rake 16 to create an even surface and begin the process of homogenizing the samples prior to measurement. The leveling rake can even out the stream such that subsequent steps can be more consistent. Utilizing a roller 6, a step 203 of further homogenizing or evenly distributing the fine crumbled root crop pieces 24 in the stream is carried out. This step can also include cleaning the roller and/or transporting device of adhered residual crop pieces through the use of one or more scrapers to avoid redepositing and contaminating subsequent material samples which follow. Subsequently, an irradiating step 204 of the stream with light in the near infrared range is carried out where the reflected or absorbed radiation by the fine pieces is recorded 205. This recorded radiation is converted 206 into a spectral signal, and processing 207 of the spectral signal can then determine the components of the root crops.

Method 200 can be performed in a quality lab. Alternatively, method 200 can be performed in a factory setting by providing a shunted or diverted stream of root crops from the factory production line to device 1, before the root crop is cut into pieces or cossettes in the factory for processing into the final product. Alternately, the root crops can be first cut into pieces or cossettes in the factory environment, and then method 200 may comprise steps 204, 205, 206 and 207, optionally or additionally step 203, and optionally or additionally step 202. These steps can be performed in-line with the factory production line itself or via a shunted or diverted stream to measure one or more of the properties of the root crop as described above. In many cases the analyzed root crops can then be reclaimed and used to produce a product using normal procedures.

When performed at a factory setting as part of an industrial process, information about the determined components in a root crop stream can often be used to modify production parameters to improve the efficiency or yield of the process. These parameters can include process temperature, conveying speed, and/or duration in a reactor. Additionally, further parameters can include the application of milk of lime and $CO_2$ in raw juice purification, or the adjustment of the processes of liming, carbonation, sludge separation, and/or sulphuration in juice purification process.

Some or all steps of the method can also be implemented at other locations, such as at a piler station. When root crops such as sugar beets are harvested, they are typically hauled to a remote receiving site. At the receiving site, the trucks can be unloaded onto a piler, which collects the crops received from the various transport vehicles. The piler can remove soil and other non-crop material debris and then sort the crops into piles. The piles are often held prior to shipment to a production facility pending the lab results of the crop components. Implementing some or all of the determination steps at the piler station can expedite this process.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In describing example embodiments, terminology has been resorted to for the sake of clarity. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology. For clarity and conciseness, not all possible combinations have been listed, and such variants are often apparent to those of skill in the art and are intended to be within the scope of the claims which follow.

The invention claimed is:

1. A device for crumbling root crops into a stream of substantially equal sized pieces, comprising:
    a main frame having an inlet side and an outlet side;
    a hopper proximate to the inlet side for collecting root crops;
    a leveling rake proximate to the outlet side for leveling a stream of root crop pieces;
    at least one crumbling shaft rotatably supported in the main frame, the crumbling shaft comprising a plurality of curved hooks;
    a non-rotating cutting rake comprising a plurality of recesses forming a counter blade for the curved hooks; and
    a cleaning rake opposite the cutting rake, the cleaning rake comprising a sloped upper comb and a plurality of recesses for stripping off root crop pieces from the hooks; the hooks arranged for interlaced movement with said recesses of the cutting rake and said recesses of the cleaning rake.

2. The device of claim 1, the sloped upper comb of the cleaning rake comprising an angle relative to a side panel of the main frame.

3. The device of claim 2, the angle being approximately 45 degrees.

4. The device of claim 1, the cleaning rake further comprising a lower toe extension forming an angle relative to a side panel of the main frame.

5. The device of claim 1, the leveling rake comprising a substantially L-shaped cross section.

6. The device of claim 1, the leveling rake comprising a polymeric non-stick material.

7. The device of claim 1, further comprising a transport device approximate the outlet side of the main frame for moving the stream of root crop pieces.

8. The device of claim 7, the transport device comprising a conveyor belt.

9. The device of claim 7, the leveling rake being adjustable in height for adjusting a vertical distance to said transport device.

10. The device of claim 7, further comprising a rolling element rotatable to compress the stream of root crop pieces.

11. The device of claim 10, the rolling element positioned a vertical distance from said transport device.

12. The device of claim 11, said vertical distance comprising a range between approximately 100 mm and approximately 150 mm.

13. The device of claim 10, further comprising a scraper positioned above the rolling element to remove residual pieces of root crop adhered to the rolling element as the rolling element rotates.

14. The device of claim 13, the scraper oriented at an oblique angle relative to a longitudinal axis of the rolling element.

15. A method for determining components in root crops, the method comprising the steps of:
    crumbling the root crops into substantially equal sized fine pieces using a device for crumbling root crops according to claim 1;
    generating a stream of fine pieces of root crops, and transporting the stream of fine pieces of root crops with the aid of a transport device;
    uniformly level the stream of fine pieces of root crops with the aid of a leveling rake positioned above the transport device;
    homogenizing or evenly distributing the stream of fine pieces of root crops by compressing them beneath a rotatable rolling element;
    irradiating the stream of fine pieces of root crop with light in the near infrared range;
    recording the reflected and/or absorbed radiation;
    converting radiation into a spectral signal; and
    processing of the spectral signal for determination of the components.

16. The method of claim 15, further comprising evenly supplying root crops to the device for crumbling root crops, such that the root crops are free to move and spring in the device.

17. The method of claim 16, further comprising cleaning a rolling element of the device for crumbling root crops of residual adhered root crop pieces through a stationary scraper and depositing the residual adhered root crop pieces outside of the stream of root crop pieces to be irradiated.

18. The method of claim 15, wherein the components are determined during an industrial production process of root crops in a production facility.

19. The method of claim 18, further comprising producing a product from root crops derived from a same source as the stream of fine pieces of root crops.

20. The method of claim 19, wherein determined components of the root crops are used to change at least one production parameter in the industrial production process of the product.

21. The method of claim 15, wherein the components are determined at a piler station.

* * * * *